United States Patent
Mitsuoka et al.

(10) Patent No.: US 11,034,637 B2
(45) Date of Patent: Jun. 15, 2021

(54) SOLVENT COMPOSITION, CLEANING METHOD, METHOD OF FORMING A COATING FILM, HEAT TRANSFER FLUID, AND HEAT CYCLE SYSTEM

(71) Applicant: AGC Inc., Chiyoda-ku (JP)

(72) Inventors: Hiroaki Mitsuoka, Chiyoda-ku (JP); Toshio Miki, Chiyoda-ku (JP); Masahiko Nakamura, Chiyoda-ku (JP); Mari Ichinokawa, Chiyoda-ku (JP); Hidekazu Okamoto, Chiyoda-ku (JP); Atsushi Fujimori, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/864,425

(22) Filed: May 1, 2020

(65) Prior Publication Data

US 2020/0255361 A1 Aug. 13, 2020

Related U.S. Application Data

(63) Continuation of application No. 16/035,071, filed on Jul. 13, 2018, now Pat. No. 10,683,249, which is a continuation of application No. PCT/JP2017/001082, filed on Jan. 13, 2017.

(30) Foreign Application Priority Data

Jan. 15, 2016 (JP) .................. 2016-005952

(51) Int. Cl.
| | | |
|---|---|---|
| *C07C 19/10* | (2006.01) | |
| *C11D 7/50* | (2006.01) | |
| *C09D 201/00* | (2006.01) | |
| *C09D 7/20* | (2018.01) | |
| *C09D 7/48* | (2018.01) | |
| *C09K 5/04* | (2006.01) | |
| *B08B 3/08* | (2006.01) | |

(52) U.S. Cl.
CPC ............... *C07C 19/10* (2013.01); *C09D 7/20* (2018.01); *C09D 7/48* (2018.01); *C09D 201/00* (2013.01); *C09K 5/044* (2013.01); *C11D 7/50* (2013.01); *C11D 7/5018* (2013.01); *B05D 2401/10* (2013.01); *B08B 3/08* (2013.01); *C09K 2205/126* (2013.01)

(58) Field of Classification Search
CPC ......... C07C 19/10; C11D 7/5018; C11D 7/50; C09D 7/48; C09D 7/20; C09D 7/40; C09D 201/00; C09K 5/044; C09K 5/04; C09K 2205/126; B05D 7/00; B05D 2401/10; B08B 3/08
USPC ..................... 252/364, 67, 68, 69
See application file for complete search history.

(56) References Cited

U.S. PATENT DOCUMENTS

| | | | |
|---|---|---|---|
| 1,904,450 | A | 4/1933 | Harris |
| 2011/0037016 | A1* | 2/2011 | Singh ................. B01D 11/0407 252/67 |
| 2011/0312101 | A1 | 12/2011 | Tsuchiya et al. |
| 2012/0064014 | A1 | 3/2012 | Basu et al. |
| 2012/0161063 | A1* | 6/2012 | Singh ....................... C08J 9/149 252/67 |
| 2013/0161554 | A1 | 6/2013 | Elsheikh et al. |
| 2013/0165363 | A1 | 6/2013 | Decaire et al. |
| 2014/0248706 | A1 | 9/2014 | Tsuchiya et al. |
| 2015/0037505 | A1 | 2/2015 | Tsuzaki et al. |
| 2015/0231527 | A1 | 8/2015 | Singh |
| 2015/0240089 | A1 | 8/2015 | Mitsuoka et al. |
| 2016/0023974 | A1 | 1/2016 | Bonnet et al. |
| 2018/0127341 | A1 | 5/2018 | Nakamura et al. |
| 2020/0190341 | A1* | 6/2020 | Mitsuoka .................. B08B 3/08 |

FOREIGN PATENT DOCUMENTS

| | | |
|---|---|---|
| CA | 2 859 456 A1 | 6/2013 |
| CN | 105008271 | 10/2015 |
| FR | 3 003 566 A1 | 9/2014 |
| JP | 2008-531836 | 8/2008 |
| JP | 2010-531924 | 9/2010 |
| JP | 2012-506944 | 3/2012 |
| JP | 2013-504658 | 2/2013 |
| JP | 2013-224383 | 10/2013 |
| JP | 2015-508435 | 3/2015 |
| JP | 2016-514664 | 5/2016 |
| JP | 2016-160233 | 9/2016 |

(Continued)

OTHER PUBLICATIONS

Johnny Betancourt, "Degrees of Unsaturation (Organic Chemistry/Degrees-of-unsaturation)", Clutch Learning, Inc., 14 pages, 2020. (Year: 2020).*
Organic Chemistry, Morrison and Boyd, Allyn and Bacon, Inc., 3rd ed., p. 284, 1973. (Year: 1973).*
International Search Report dated Feb. 14, 2017 in PCT/JP2017/001082, filed on Jan. 13, 2017(with English Translation).

(Continued)

*Primary Examiner* — Douglas J McGinty
(74) *Attorney, Agent, or Firm* — Oblon, McClelland, Maier & Neustadt, L.L.P.

(57) ABSTRACT

The present invention is a solvent composition including: a solvent including 1-chloro-2,3,3-trifluoro-1-propene; and at least one type of stabilizer selected from a group consisting of phenols, ethers, epoxides, amines, alcohols, and hydrocarbons, and is a solvent composition which is excellent in solubility of various organic substances and has no adverse effect on a global environment, and is excellent in stability, and this solvent composition can be used for a wide range of industrial uses such as cleaning, coating uses, and a heat transfer fluid.

17 Claims, No Drawings

(56) References Cited

FOREIGN PATENT DOCUMENTS

| | | |
|---|---|---|
| JP | 2016-164152 | 9/2016 |
| WO | 2006/094303 A2 | 9/2006 |
| WO | 2009/003165 A1 | 12/2008 |
| WO | 2010/062572 A2 | 6/2010 |
| WO | 2010/098451 A1 | 9/2010 |
| WO | 2011/031697 A2 | 3/2011 |
| WO | 2013/096742 A1 | 6/2013 |
| WO | 2013/161723 A1 | 10/2013 |
| WO | 2014/073372 A1 | 5/2014 |
| WO | 2014/147311 A1 | 9/2014 |
| WO | 2015/060261 A1 | 4/2015 |
| WO | 2016/136744 A1 | 9/2016 |

OTHER PUBLICATIONS

Written Opinion dated Feb. 14, 2017 in PCT/JP2017/001082, filed on Jan. 13, 2017.
CAS reg. No. 1263679-68-0, Feb. 23, 2011, (Year: 2011).

\* cited by examiner

SOLVENT COMPOSITION, CLEANING METHOD, METHOD OF FORMING A COATING FILM, HEAT TRANSFER FLUID, AND HEAT CYCLE SYSTEM

CROSS-REFERENCE TO RELATED APPLICATIONS

This application is a continuation of U.S. application Ser. No. 16/035,071, filed on Jul. 13, 2018 which is a continuation of prior International Application No. PCT/JP2017/001082, filed on Jan. 13, 2017 which is based upon and claims the benefit of priority from Japanese Patent Application No, 2016-005952, filed on Jan. 15, 2016; the entire contents of all of which are incorporated herein by reference.

FIELD

The present invention relates to a solvent composition which is excellent in solubility of various organic substances and has no adverse effect on a global environment, and is excellent in stability. Specifically, the solvent composition of the present invention can be used in a wide range of uses, such as a cleaning solvent, a coating solvent, and a heat transfer fluid.

BACKGROUND

In manufacture of IC, an electronic component, a precision machinery component, an optical component, and the like, in a manufacturing process, an assembly process, a final finishing process, and the like, components are cleaned by a cleaning solvent, thereby removing flux, a machining oil, wax, a release agent, dust, and the like adhering to the components. Further, as a method of manufacturing an article having a coating film containing various organic chemical substances such as a lubricant, for example, there is known a method in which a solution in Which the organic chemical substances have been dissolved in a coating solvent is prepared, the solution is coated on an article to be coated, and thereafter the coating solvent is evaporated to form a coating film. The coating solvent is required to allow the organic chemical substances to be dissolved sufficiently and to have a sufficient drying property as well.

As a solvent to be used in such uses, in that it has incombustibility and low toxicity, is excellent in stability, does not encroach on a base material of metal, plastic, elastomer, or the like, and is excellent in chemical and thermal stability, there has been used a fluorine-based solvent or the like containing chlorofluorocarbons (hereinafter, mentioned as "CFCs") such as 1,1,2-trichloro-1,2,2-trifluoroethane, hydrochlorofluorocarbons (hereinafter, mentioned as "HCFCs".) such as 2,2-dichloro-1,1,1-trifluoroethane, 1,1-dichloro-1-fluoroethane, 3,3-dichloro-1,1,1,2,2-pentafluoropropane, and 1,3-dichloro-1,1,2,2,3-pentafluoropropane, or the like.

However, because the CFCs are chemically very stable, they have a long lifetime in the troposphere after vaporization, and diffuse and reach the stratosphere. Therefore, there is a problem that the CFCs which have reached the stratosphere are decomposed by ultraviolet rays and generate chlorine radicals to deplete an ozone layer. Therefore, production of the CFCs is regulated on a global scale, and the production in developed countries is already completely abolished.

Further, because the HCFCs also have chlorine atoms and affect the ozone layer slightly but adversely, production thereof is to be abolished completely in developed countries in 2020.

On the other hand, as a solvent having no chlorine atom and having no adverse effect on the ozone layer, perfluorocarbons (hereinafter, mentioned as "PFCs".) are known. In addition, as alternative solvents to the CFCs and the HCFCs, hydrofluorocarbons (hereinafter, mentioned as "HFCs".), hydrofluoroethers (hereinafter, mentioned as "HFEs".), and the like are also under development.

However, the HFCs and the PFCs are substances subject to regulation by the Kyoto Protocol in order to prevent global warming.

As new solvents substituted for the solvents of the HFCs, the HFEs, and the PFCs, fluoroolefins each having a double bond between carbon atoms are proposed. These fluoroolefins each have a short lifetime in the atmosphere due to easy decomposition, their ozone depletion potential and global warming potential are low, and they have an excellent property in Which an effect on a global environment is small, but on the other hand, they are poor in stability due to the easy decomposition, and there has been a problem that in a case of use as the cleaning solvent or the coating solvent, they decompose and acidify in use.

As such fluoroolefins poor in the stability, there is 1,1-dichloro-2,3,3,3-tetrafluoropropene in References 1 and 2 (JP-A 2013-224383 and WO 2013/161723 A1), and stabilization techniques as mentioned in References 3 and 4 (WO 2014/073372 A1 and WO 2015/060261 A1) are demonstrated.

Other than References 3 and 4, examples of techniques of stabilizing fluoroolefin having a double bond between carbon atoms are also disclosed (References 5, 6, and 7 JP-A 2008-531836, WO 2010/098451 A1 and JP-A 2010-531924), but are not each a technique of stabilizing all of fluoroolefins, and the techniques of stabilization are different depending on a type of fluoroolefin or a purpose of use.

Thus, it is known that the techniques for stabilization are different depending on the type of fluoroolefin. Even if the techniques mentioned in the prior art documents are applied, it is not possible to predict whether or not a stabilization effect with respect to 1-chloro-2,3,3-trifluoro-1-propene is obtained.

SUMMARY

In the present invention, it is an object thereof to provide: a solvent composition which is excellent in solubility of various organic substances and has no adverse effect on a global environment, and is excellent in stability; a cleaning method using the solvent composition; a method of forming a coating film using the solvent composition; a heat transfer fluid including the solvent composition; and a heat cycle system using the heat transfer fluid.

The present inventors have performed studies in consideration of the above-described points, resulting in completing the present invention. That is, the present invention is as follows.

[1] A solvent composition including: 1-chloro-2,3,3-trifluoro-1-propene; and at least one type of stabilizer selected from a group consisting of phenols, ethers, epoxides, amines, alcohols, and hydrocarbons.

[2] The solvent composition according to [1], wherein a content of the stabilizer is from 1 mass ppm to 10 mass % in the solvent composition (100 mass %).

[3] The solvent composition according to [1] or [2], wherein a content of 1-chloro-2,3,3-trifluoro-1-propene is 80 mass % or more in the solvent composition (100 mass %).

[4] The solvent composition according to any one of [1] to [3], wherein the 1-chloro-2,3,3-trifluoro-1-propene is a mixture of a Z-isomer of 1-chloro-2,3,3-trifluoro-1-propene and an E-isomer of 1-chloro-2,3,3-trifluoro-1-propene, and wherein a content proportion of the Z-isomer of 1-chloro-2,3,3-trifluoro-1-propene to a total amount of the Z-isomer of 1-chloro-2,3,3-trifluoro-1-propene and the E-isomer of 1-chloro-2,3,3-trifluoro-1-propene is 80 mass % or more and less than 100 mass %.

[5] The solvent composition according to any one of [1] to [4], wherein a boiling point of the stabilizer is 30 to 120° C.

[6] The solvent composition according to [5], wherein the stabilizer includes at least one selected from methanol, ethanol, isopropanol, 2-propyn-1-ol, 1,2-butylene oxide, tetrahydrofuran, 1,4-dioxane, n-propylamine, diisopropylamine, N-methylmorpholine, N-methylpyrrole, 2-methyl-2-butene, 2-methyl-1-pentene, 2-methyl-2-pentene, 3-ethyl-2-butene, 2,3-dimethyl-2-butene, 2,4,4-trimethyl-1-pentene, 2,4,4-trimethyl-2-pentene, and n-heptane.

[7] A cleaning method including cleaning an article to be cleaned by using the solvent composition according to any one of [1] to [6].

[8] The cleaning method according to [7], wherein an article to be cleaned is at least one type selected from a fiber product, a medical appliance, electric equipment, a precision instrument, and an optical article.

[9] A method of forming a coating film including dissolving a nonvolatile substance in the solvent composition according to any one of [1] to [6], coating an obtained composition of a nonvolatile substance on an article to be coated, and evaporating the solvent composition, to form a coating film having the nonvolatile substance as a main component.

[10] A heat transfer fluid including the solvent composition according to any one of [1] to [6].

[11] A heat cycle system using the heat transfer fluid according to [10].

A solvent composition of the present invention is excellent in solubility of various organic substances and has no adverse effect on a global environment, and is excellent in stability.

A cleaning method of the present invention has no adverse effect on a global environment and is excellent in detergency.

A method of forming a coating film of the present invention has no adverse effect on a global environment and allows a uniform coating film to be formed.

A heat transfer fluid including the solvent composition of the present invention has no adverse effect on a global environment and is excellent in stability.

A heat cycle system using the heat transfer fluid of the present invention has no adverse effect on a global environment.

DETAILED DESCRIPTION

A solvent composition of the present invention is a solvent composition including 1-chloro-2,3,3-trifluoro-1-propene (hereinafter mentioned as "HCFO-1233yd".) and at least one type of stabilizer selected from a group consisting of phenols, ethers, epoxides, amines, alcohols, and hydrocarbons. Hereinafter, a solvent composition which is one embodiment of the present invention will be explained.

In this embodiment, HCFO-1233yd may be any of HCFO-1233yd(Z), HCFO-1233yd(E), and a mixture of HCFO-1233yd(Z) and HCFO-1233yd(E).

<HCFO-1233yd>

Because HCFO-1233yd is fluoroolefin having a double bond between carbon atoms, its lifetime in the atmosphere is short and its ozone depletion potential and global warming potential are low.

In HCFO-1233yd, structural isomers of a Z-isomer (hereinafter mentioned as "HCFO-1233yd(Z)") and an E-isomer (hereinafter mentioned as "HCFO-1233yd(E)") exist.

A boiling point of HCFO-1233yd(Z) is about 54° C., a boiling point of HCFO-1233yd(E) is 48° C., and both are substances excellent in a drying property.

Further, even though they are boiled to turn into vapor, even parts susceptible to heat, such as resin parts, are not easily adversely affected since the boiling point of HCFO-1233yd(Z) is about 54° C. and the boiling point of HCFO-1233yd(E) is 48° C. In addition, HCFO-1233yd has excellent ability, such as no flash point, low surface tension and viscosity, excellent permeability, and easy evaporation even at room temperature, as a cleaning solvent or a coating solvent.

From practical handling easiness as the cleaning solvent or the coating solvent and economic superiority to be considered from the boiling points and production easiness, for the solvent composition of the present invention, HCFO-1233yd is suitable, and further, of two types of structural isomers of HCFO-1233yd, HCFO-1233yd(Z) is preferable. However, HCFO-1.233yd is poor in stability in the air, and there is a problem that HCFO-1233yd decomposes in several days to generate chlorine ions when stored under the boiling point of HCFO-1233yd.

HCFO-1.233yd can be manufactured by subjecting, for example, industrially stably obtainable 1-chloro-2,2,3,3-tetrafluoropropane (HCFO-244ca) to a dehydrofluorination reaction. According to this method, HCFO-1233yd is produced by subjecting HCFO-244ca to the dehydrofluorination reaction in the presence of a base.

The produced HCFO-1233yd is obtained as the mixture of HCFO-1233yd(Z) and HCFO-1233yd(E) which are structural isomers. In addition, in this production example, HCFO-1233yd(Z) is produced more than HCFO-1233yd(E). These isomers can be separated in a purification process thereafter. HCFO-1233yd(Z) obtained in this production example sometimes contains HCFO-244ca or HCFO-1233yd(E) which is a substance deriving from a raw material, 1,1,2-trifluoro-3-chloropropene (HCFO-1233yc), or 1-chloro-3,3-difluoropropyne.

A purity of HCFO-1233yd in this embodiment is preferably 99 mass % or more and more preferably 99.5 mass % or more.

An amount of HCFO-1233yd in the solvent composition (100 mass %) of this embodiment is preferably 80 to 99.9999 mass % and is preferably 90 to 99.9995 mass %. By being in the above-described range, the solvent composition is excellent in solubility of various organic substances.

In the solvent composition of this embodiment, in HCFO-1233yd. HCFO-1233yd(Z) or HCFO-1233yd(E) may be used alone, and the mixture of HCFO-1233yd(Z) and HCFO-1233yd(E) may be used.

When the mixture of HCFO-1233yd(Z) and HCFO-1233yd(E) is used, a content proportion of HCFO-1233yd (Z) with respect to a total amount of HCFO-1233yd(Z) and HCFO-1233yd(E) is preferably 80 mass % or more and less than 100 mass %, more preferably not less than 90 mass % nor more than 99 mass %, and further preferably not less than 95 mass % nor more than 98 mass %, The boiling point of HCFO-1233yd(E) is higher than that of HCFO-1233yd (Z), and therefore, as long as the content proportion of HCFO-1233yd(Z) is equal to or more than the above-described lower limit value, the solvent composition is easy to practically handle as the cleaning solvent or the coating solvent thereof.

The present inventor and the like have studied, and as a result, found that the solvent composition of this embodiment includes HCFO-1233yd and at least one type of stabilizer selected from a group consisting of phenols, ethers, epoxides, amines, alcohols, and hydrocarbons, thereby making it possible to suppress decomposition of HCFO-1233yd and making the solvent composition stabilize.

The stabilizer in this embodiment means the one having an effect of suppressing decomposition of HCFO-1233yd(Z) and HCFO-1233yd(E).

Here, the stability can be evaluated by, for example, providing a chlorine ion concentration after retaining a test solution in which the stabilizer has been dissolved in a predetermined proportion in HCFO-1233yd for a certain period as an index. The chlorine ion concentration is measured by an ion chromatograph.

Specifically, as the stabilizer in the solvent composition of this embodiment, in retaining HCFO-1233yd at 50° C. for three days, a stabilizer in which the chlorine ion concentration in the solvent composition becomes 100 ppm or less is preferable, a stabilizer in which the chlorine ion concentration becomes 50 ppm or less is more preferable, and a stabilizer in which the chlorine ion concentration becomes 10 ppm or less is further preferable.

A content of the stabilizer in the solvent composition of this embodiment is preferably 1 mass ppm or more, more preferably 5 mass ppm or more, and particularly preferably 10 mass ppm or more with respect to the solvent composition. In addition, the content of this stabilizer is preferably 10 mass % or less, more preferably 5 mass % or less, and particularly preferably 1 mass % or less. The stabilizer is particularly excellent in that not only the stability with respect to HCFO-1233yd is exhibited sufficiently but also properties of low surface tension and viscosity and good permeability which HCFO-1233yd has are not impaired as long as it is in the above-described preferable range.

In the stabilizer in this embodiment, stabilizing actions are considered to be different from each other. For example, the phenols and the hydrocarbons suppress the decomposition of HCFO-1233yd by an oxidation-preventing action, and the epoxides capture generated acid and chlorine ions, and further, the amines neutralize acidic substances caused by the decomposition, whereby the respective stabilizers are presumed to suppress decomposition promotion of HCFO-1233yd due to the acidic substances. Accordingly, by containing two or more types of stabilizers as necessary, a synergistic effect of each of the stabilizers is obtained.

The phenols in this embodiment mean aromatic hydroxy compounds each having one or more hydroxy groups on an aromatic hydrocarbon nucleus. The aromatic hydroxy compounds are preferably dissolved in HCFO-1233yd. The aromatic hydrocarbon nucleus is preferably a benzene nucleus. One or more substituents may be bonded to the aromatic hydrocarbon nucleus other than hydrogen atoms. As the substituent, a hydrocarbon group, an alkoxy group, an acyl group, a carbonyl group, and so on can be cited. Further, halogen atoms may be substituted for one or more hydrogen atoms bonded to the aromatic hydrocarbon nucleus. As the hydrocarbon group, an alkyl group, an alkenyl group, an aromatic hydrocarbon group, an aralkyl group, and so on can be cited.

Among these, the number of carbon atoms of each of the alkyl group, the alkenyl group, the alkoxy group, an acyl group, and the carbonyl group is preferably 6 or less, and the number of carbon atoms of each of the aromatic hydrocarbon group and the aralkyl group is preferably 10 or less. As the hydrocarbon group, the alkyl group or the alkenyl group is preferable, and the alkyl group is particularly preferable. Furthermore, it is preferable to have the alkyl group or the alkoxy group in an ortho position with respect to a hydroxy group of the aromatic hydrocarbon nucleus. As the alkyl group in the ortho position, a branched alkyl group such as a tert-butyl group is preferable. When two ortho positions exist, the alkyl groups may exist on both of them.

As the phenols, specifically, there can be cited phenol, 1,2-benzenediol, 1,3-benzenediol, 1,4-benzenediol, 1,3,5-benzenetriol, 2,6-di-tert-butyl-4-methylphenol, 2,4,6-tri-tert-butylphenol, 2-tert-butylphenol, 3-tert-butylphenol, 4-tert-butylphenol, 2,4-di-tert-butylphenol, 2,6-di-tert-butylphenol, 4,6-di-tert-butylphenol, o-cresol, m-cresol, p-cresol, 2,3-dimethylphenol, 2,4-dimethylphenol, 2,5-dimethylphenol, 2,6-dimethylphenol, 2,3,6-trimethylphenol, 2,4,6-trimethylphenol, 2,5,6-trimethylphenol, 3-isopropylphenol, 2-isopropyl-5-methylphenol, 2-methoxyphenol, 3-methoxyphenol, 4-methoxyphenol, 2-ethoxyphenol, 3-ethoxyphenol, 4-ethoxyphenol, 2-propoxyphenol, 3-propoxyphenol, 4-propoxyphenol, α-tocopherol, β-tocopherol, γ-tocopherol, and 4-tert-butylcatechol.

Among them, phenol, 1,2-benzenediol, 2,6-di-tert-butyl-4-methylphenol, m-cresol, 2-isopropyl-5-methylphenol, α-tocopherol, and 2-methoxyphenol are more preferable.

A content of the above-described phenols in the solvent composition of this embodiment is preferably 1 mass ppm to 10 mass %, more preferably 5 mass ppm to 5 mass %, and further preferably 10 mass ppm to 1 mass % with respect to the solvent composition of this embodiment. The phenols are particularly excellent in that the sufficient stability with respect to HCFO-1233yd is exhibited and in addition, the properties of low surface tension and viscosity and good permeability which HCFO-1233yd has are not impaired as long as their content is in the above-described preferable range.

Further, the ethers in this embodiment mean chain ether in which two hydrocarbon groups are bonded to an oxygen atom and cyclic ether (however, an epoxy ring which is a 3-membered cyclic ether is excepted) having an oxygen atom as an atom constituting a ring. The number of ether oxygen atoms in the chain ether and the cyclic ether may be 2 or more. The number of carbon atoms in the ethers is preferably 12 or less. Further, carbon atoms of the hydrocarbon groups constituting ether may each have a substituent such as a halogen atom or a hydroxy group. However, the ethers each having an epoxy group are regarded as the epoxides.

As the ethers, specifically, there can be cited dimethyl ether, diethyl ether, dipropyl ether, diisopropyl ether, dibutyl ether, dipentyl ether, diisopentyl ether, diallyl ether, ethyl methyl ether, ethyl propyl ether, ethyl isopropyl ether, ethyl isobutyl ether, ethyl isopentyl ether, ethyl vinyl ether, allyl ethyl ether, ethyl phenyl ether, ethyl naphthyl ether, ethyl propargyl ether, 1,4-dioxane, 1,3-dioxane, 1,3,5-trioxane, ethylene glycol monomethyl ether, ethylene glycol monobutyl ether, ethylene glycol monophenyl ether, ethylene glycol monobenzyl ether, ethylene glycol dimethyl ether, ethylene glycol diethyl ether, ethylene glycol diphenyl ether, diethylene glycol monomethyl ether, diethylene glycol monoethyl ether, dipropylene glycol methyl ether, anisole, anethole, trimethoxyethane, triethoxyethane, furan, 2-methylfuran, and tetrahydrofuran.

As the ethers, cyclic ethers each having 4- to 6-membered ring are preferable, and among them, 1,4-dioxane, 1,3-dioxane, 1,3,5-trioxane, 2-methylfuran, and tetrahydrofuran are preferable.

A content of the above-described ethers in the solvent composition of this embodiment is preferably 1 mass ppm to 10 mass %, more preferably 10 mass ppm to 7 mass %, and further preferably 0.01 mass % to 5 mass % with respect to the solvent composition of this embodiment. The ethers are particularly excellent in that the sufficient stability with respect to HCFO-1233yd is exhibited and in addition, the properties of low surface tension and viscosity and good permeability which HCFO-1233yd has are not impaired as long as their content is in the above-described preferable range.

Further, the epoxides in this embodiment mean compounds each having one or more epoxy groups which are the 3-membered cyclic ether. The epoxides may each have 2 or more epoxy groups in one molecule, and further may each have a substituent such as a halogen atom, an ether oxygen atom, or a hydroxy group. The number of carbon atoms in the epoxides is preferably 12 or less.

As the epoxides, specifically, there can be cited 1,2-propylene oxide, 1,2-butylene oxide, 1,2-epoxy-3-phenoxypropane, -butyl glycidyl ether, methyl glycidyl ether, ethyl glycidyl ether, butyl glycidyl ether, vinyl glycidyl ether, allyl glycidyl ether, diethylene glycol diglycidyl ether, epichlorohydrin, d-limonene oxide, and 1-limonene oxide. Among them, 1,2-propylene oxide, 1,2-butylene oxide, and butyl glycidyl ether are preferable.

A content of the above-described epoxides in the solvent composition of this embodiment is preferably 1 mass ppm to 10 mass %, more preferably 10 mass ppm to 7 mass %, and further preferably 0.01 mass % to 5 mass % with respect to the solvent composition of this embodiment. The epoxides are particularly excellent in that the sufficient stability with respect to HCFO-1233yd is exhibited and in addition, the properties of low surface tension and viscosity and good permeability which HCFO-1233yd has are not impaired as long as their content is in the above-described preferable range.

Further the amines in this embodiment mean compounds (primary to tertiary amines) each having one or more substituted or unsubstituted amino groups. In addition, the amines may be non-cyclic amines or cyclic amines (cyclic compounds in each of which a nitrogen atom of an amino acid is an atom constituting a ring), As groups bonded to a nitrogen atom of each of secondary amine and tertiary amine, an alkyl group or a hydroxyalkyl group having 6 or less carbon atoms is preferable. An aliphatic amine or an aromatic amine can be cited as the non-cyclic amines. A benzene nucleus-containing compound having one or more substituted or unsubstituted amino groups can be cited as the aliphatic amine. As the cyclic amines, 4- to 6-membered ring compounds in each of which the number of nitrogen atoms constituting a ring is 1 to 3 can be cited. Further, the number of carbon atoms in the amines is preferably 16 or less and more preferably 10 or less.

As the amines, specifically, there can be cited methylamine, dimethylamine, trimethylamine, ethylamine, diethylamine, triethylamine, n-propylamine, di-n-propylamine, isopropylamine, diisopropylamine, butylamine, dibutylamine, tributylamine, isobutylamine, diisobutylamine, secondary-butylamine, tert-butylamine, pentylamine, dipentylamine, tripentylamine, hexylamine, 2-ethylhexylamine, allylamine, diallylamine, triallylamine, aniline, N-methylaniline, N,N-dimethylaniline, N,N-diethylaniline, pyridine, picoline, morpholine, N-methylmorpholine, benzylamine, dibenzylamine, α-methylbenzylamine, propylene diamine, diethylhydroxyamine, pyrrole, N-methylpyrrole, 2-methylpyridine, 3-methylpyridine, 4-methylpyridine, ethanolamine, diethanolamine, triethanolamine, propanolamine, dipropanolamine, isopropanolamine, diisopropanolamine, N-methylethanolamine, N,N-dimethylethanolamine, N-ethylmorpholine, diphenylamine, and ethylenediamine.

As the amines, alkylamine and cyclic amines are preferable, and among them, pyrrole, N-methylpyrrole, 2-methylpyridine, n-propylamine, diisopropylamine, N-methylmorpholine, and N-ethylmorpholine are preferable.

A content of the above-described amities in the solvent composition of this embodiment is preferably 1 mass ppm to 10 mass %, more preferably 5 mass ppm to 5 mass %, further preferably 10 mass ppm to 1 mass %, and the most preferably 0.001 to 0.1 mass % with respect to the solvent composition of this embodiment. The amines are particularly excellent in that the sufficient stability with respect to HCFO-1233yd is exhibited and in addition, the properties of low surface tension and viscosity and good permeability which HCFO-1233yd has are not impaired as long as their content is in the above-described preferable range.

Furthermore, because the above-described amines have a buffering action, there is an effect of capturing acid to be generated when HCFO-1233yd dissolves, preventing acid content increase, and suppressing a further decomposition reaction, and an influence due to an external factor can be reduced by capturing an acid content brought in from the exterior.

Further, the alcohols in this embodiment mean organic compounds in each of which a hydroxy group is bonded to hydrocarbon having a linear, branched-chain, or cyclic structure. As the alcohols in this embodiment, owing to characteristics of having solubility to HCFO-1233yd, having volatility, and having difficulty in remaining on a surface of an article by volatilizing with HCFO-1233yd, the alcohols each having 1 to 3 carbon atoms are preferable.

As the alcohols, specifically, there can be cited methanol, ethanol, 1-propanol, isopropanol, 1-butanol, 2-butanol, 2-methyl-1-propanol, 2-methyl-2-propanol, 1-pentanol, 2-pentanol, 1-ethyl-1-propanol, 2-methyl-1-butanol, 3-methyl-1 butanol, 3-methyl-2-butanol, neopentyl alcohol, 1-hexanol, 2-ethyl-1-pentanol, 4-methyl-2-pentanol, 2-ethyl-1-butanol, 1-heptanol, 2-heptanal, 3-heptanol, 1-octanol, 2-octanol, 2-ethyl-1-hexanol, 1-nonanol, 3,5,5-trimethyl-1-hexanol, 1-decanol, 1-undecanol, 1-dodecanol, allyl alcohol, benzyl alcohol, cyclohexanol, 1-methylcyclohexanol, 2-methylcyclohexanol, 3-methylcyclohexanol, 4-methylcyclohexanol, α-terpineol, 2,6-dimethyl-4-heptanol, nonyl alcohol, tetradecyl alcohol, 2-propyn-1-ol, and so on. Among them, methanol, ethanol, isopropanol, and 2-propyn-1-ol which are linear or branched-chain alcohols each having 1 to 3 carbon atoms are more preferable.

A content of the above-described alcohols in the solvent composition of this embodiment is preferably 1 mass ppm to 10 mass %, more preferably 5 mass ppm to 5 mass %, further preferably 10 mass ppm to 1 mass % (0, and the most preferably 0.001 to 0.1 mass % with respect to the solvent composition of this embodiment. The alcohols are particularly excellent in that the sufficient stability with respect to HCFO-1233yd is exhibited and in addition, the properties of low surface tension and viscosity and good permeability which HCFO-1233yd has are not impaired as long as their content is in the above-described preferable range.

Further, the hydrocarbons in this embodiment are organic compounds each having a hydrocarbon molecule with a linear, branched-chain, or cyclic structure. In this embodiment, the hydrocarbons may each be a saturated hydrocarbon or may be an unsaturated hydrocarbon in which at least one of carbon-carbon bonds is an unsaturated bond. As the hydrocarbons in this embodiment, in terms of having solubility to HCFO-1233yd, having volatility, and having difficulty in remaining on a surface of an article by volatilizing with HCFO-1233yd, chain or cyclic hydrocarbons each having 5 to 9 carbon atoms are preferable.

As saturated hydrocarbons, specifically, there can be cited n-pentane, n-hexane, 2-methylpentane, 3-methylpentane, 2,2-dimethylbutane, 2,3-dimethylbutane, n-heptane, 2-methylhexane, 3-methylhexane, 2,4-dimethylpentane, 2-methylheptane, 3-methylheptane, 4-methylheptane, 2,2-dimethylhexane, 2,5-dimethylhexane, 3,3-dimethylhexane, 2-methyl-3-ethylpentane, 3-methyl-3-ethylpentane, 2,3,3-trimethylpentane; 2,3,4-trimethylpentane, 2,2,3-trimethylpentane; 2-methylheptane, 2,2,4-trimethylpentane; cyclopentane; methylcyclopentane, cyclohexane, methylcyclohexane, and so on. Among them, n-pentane, cyclopentane, n-hexane, cyclohexane, and n-heptane are more preferable.

As unsaturated hydrocarbons, specifically, there can be cited a pentene isomer such as 1-pentene, 2-pentene, 2-methyl-1-butene, 3-methyl-1-butene, or 2-methyl-2-butene, a hexene isomer such as 1-hexene, 2-hexene, 3-hexene, 2-methyl-1-pentene, 3-methyl-1-pentene, 4-methyl-1-pentene, 2-ethyl-1-butene, 3-ethyl-1-butene, 3-ethyl-2-butene, 2-methyl-2-pentene, 3-methyl-2-pentene, 4-methyl-2-pentene, or 2,3-dimethyl-2-butene, a heptene isomer such as 1-heptene, 2-heptene, 3-heptene, 4-heptene, or 3-ethyl-2-pentene, an octene isomer such as 1-octene, 2,4,4-trimethyl-1-pentene, or 2,4,4-trimethyl-2-pentene, a nonene isomer such as 1-nonene, and further a diene compound such as butadiene, isoprene, hexadiene, heptadiene, or octadiene, and an unsaturated cyclic compound such as cyclohexene, cyclohexadiene, cycloheptene, cycloheptadiene, cyclooctene, or cyclooctadiene. In this embodiment, in particular, 2-methyl-2-butene, 2-methyl-1-pentene, 2-methyl-2-pentene, 3-ethyl-2-butene, 2,3-dimethyl-2-butene, 2,4,4-trimethyl-1-pentene, and 2,4,4-trimethyl-2-pentene are preferable.

Among the above-described hydrocarbons, because the unsaturated hydrocarbon has a higher oxidation preventing action by oxygen capture than that of the saturated hydrocarbon, the unsaturated hydrocarbon is more preferable as the stabilizer of HCFO-1233yd.

A content of the above-described hydrocarbons in the solvent composition of this embodiment is preferably 1 mass ppm to 10 mass %, more preferably 5 mass ppm to 7 mass %, further preferably 10 mass ppm to 5 mass %, and the most preferably 0.001 to 0.1 mass % with respect to the solvent composition of this embodiment. The hydrocarbons are particularly excellent in that the sufficient stability with respect to HCFO-1233yd is exhibited and in addition, the properties of low surface tension and viscosity and good permeability Which HCFO-1233yd has are not impaired as long as their content is in the above-described preferable range.

The solvent composition of this embodiment preferably includes at least one type of stabilizer whose boiling point is 30 to 120° C. At least one type of the above-described stabilizer among the stabilizers with a boiling point of 30 to 120° C. is included, thereby resulting in an excellent drying property. This prevents components deriving from the solvent composition of this embodiment from remaining on an article surface after cleaning or a coating firm formed on an article surface.

As a preferable stabilizer from this viewpoint, there can be cited methanol (boiling point: 64.5° C.), ethanol (boiling point: 78.4° C.), isopropanol (boiling point: 84° C.), 2-propyn-1-ol (boiling point: 112° C.), 1,2-butylene oxide (boiling point: 63.2° C.), tetrahydrofuran (boiling point: 66° C.), 1,4-dioxane (boiling point: 101° C.), n-propylamine (boiling point: 48° C.), diisopropylamine (boiling point: 84° C.), N-methylmorpholine (boiling point: 115° C.), N-methylpyrrole (boiling point: 112° C.), 2-methyl-2-butene (boiling point: 39° C.), 2-methyl-1-pentene (boiling point: 62° C.), 2-methyl-2-pentene (boiling point: 67° C.), 3-ethyl-2-butene (boiling point: 73° C.), 2,3-dimethyl-2-butene (boiling point: 73° C.), 2,4,4-trimethyl-1-pentene (boiling point: 112° C.), 2,4,4-trimethyl-2-pentene (boiling point: 112° C.), and n-heptane (boiling point: 98° C.).

Among them, in terms of stability of the solvent composition, ethanol, isopropanol, 2-propyn-1-ol, 2-methyl-1-pentene, 2-methyl-2-pentene, 3-ethyl-2-butene, 2,3-dimethyl-2-butene, 2,4,4-trimethyl-1-pentene, 2,4,4-trimethyl-2-pentene, and N-methylpyrrole are more preferable, and 2-propyn-1-ol, 2-methyl-1-pentene, 2-methyl-2-pentene, 3-ethyl-2-butene, 2,3-dimethyl-2-butene, 2,4,4-trimethyl-1-pentene, 2,4,4-trimethyl-2-pentene, and N-methylpyrrole are further preferable. By using the above-described compounds as the stabilizer, the occurrence of a causative substance causing the decomposition of HCFO-1233yd, for example, a peroxide of oxygen radicals or the like is suppressed. In addition, even when the oxygen radicals occur to produce a reductant of HCFO-1233yd, oxidizing the reductant again allows production of HCFO-1233yd.

In the solvent composition of this embodiment, by containing two or more of different types of stabilizers with a boiling point of 30 to 120° C., while maintaining the excellent drying property, the stability improves further. As a combination of the stabilizers, among the alcohols, the unsaturated hydrocarbons, and the amines, a combination of two or more types of stabilizers is preferable. For example, combinations of the alcohols and the unsaturated hydrocarbons, the alcohols and the amines, and the unsaturated hydrocarbons and the amines can be cited. A plurality of compounds belonging to the same type may be contained.

As the stabilizer, it is more preferable that stabilizers are selected from at least two or more groups among the following i) group, ii) group, and iii) group to be combined. Further, the stabilizer selected from each of the groups may be one or two or more. By using these stabilizers in combination, the synergistic effect of the stabilizers results in excellent long-term stability of the solvent composition.

i) methanol, ethanol, isopropanol, and 2-propyn-1-ol ii) 2-methyl-1-pentene, 2-methyl-2-pentene, 3-ethyl-2-butene, 2,3-dimethyl-2-butene, 2,4,4-trimethyl-1-pentene, 2,4,4-trimethyl-2-pentene, and n-heptane iii) N-methylpyrrole, N-methylmorpholine, n-propylamine, and diisopropylamine When the solvent composition of this embodiment is used in a cleaning apparatus, distillation and reproduction are repeated in the cleaning apparatus or by a solvent reproducing apparatus, and therefore, the solvent composition is continuously exposed to a severe condition. Further, when the solvent composition of this embodiment is used as a coating solvent for a nonvolatile solute, in recovering the volatilized solvent composition by absorption and desorption with activated carbon, solvent components come in contact with superheated steam at a time of the desorption from the activated carbon and the solvent composition is exposed to a severe condition. Furthermore, when the solvent composition of this embodiment is used as a heat transfer fluid in a heat cycle system, the solvent composition is exposed to a severe condition under which compression and expansion are repeated. Thus, when the solvent composition of this embodiment is used for uses accompanied by a phase change in the solvent composition, the solvent composition of this embodiment preferably includes, as the stabilizer, the phenols and the stabilizer whose boiling point is 30 to 120° C.

When the solvent composition of this embodiment is in contact with copper or a copper alloy, it may contain nitro compounds or triazoles in order to avoid corrosion of the above metals. The nitro compounds are nitromethane, nitroethane, 1-nitropropane. 2-nitropropane, and 1-nitroethylene. Nitromethane or nitroethane is more preferable. The triazoles are each the one selected from 2-(2'-hydroxy-5'-methylphenyl)benzotriazole, 2-(2'-hydroxy-3'-tert-butyl-5'-methylphenyl)-5-chlorobenzotriazole, 1,2,3-benzotriazole, 1-[(N,N-bis-2-ethylhexyl)aminomethyl]benzotriazole, and so on, and 1,2,3-benzotriazole is more preferable. A content of the above-described nitro compounds or triazoles is preferably 10 mass ppm to 1 mass % with respect to the solvent composition.

The solvent composition of this embodiment may include, in addition to HCFO-1233yd, a solvent (hereinafter, mentioned as "solvent (A)".) soluble in HCFO-1233yd according to various purposes such as enhancing solubility further and regulating an evaporation rate. Note that the solvent soluble in HCFO-1233yd means a solvent which can mix and dissolve uniformly with/in HCFO-1233yd without causing two-layer separation or turbidity by stirring at normal temperature (25° C.) so as to become a desired concentration.

The solvent (A) included in the solvent composition of this embodiment may be one type or two or more types.

As the solvent (A), at least one type of solvent selected from a group consisting of hydrocarbons, alcohols, ketones, ethers, esters, chlorocarbons, HFCs, HCFOs, and CFOs is preferable.

There are compounds usable as the solvent (A) among the above-described stabilizers in this embodiment (for example, n-heptane and the like). Such a stabilizer may be contained in the solvent composition of this embodiment over a sufficient amount in order to exhibit a stabilization effect. In that case, the stabilizer with an amount over the sufficient amount in order to exhibit the stabilization effect is regarded as the solvent (A).

As the hydrocarbons which are each the solvent (A), hydrocarbons each having 5 or more carbon atoms are preferable. With the hydrocarbons each having 5 or more carbon atoms used, a chain structure or a ring structure is applicable, and further the saturated hydrocarbons or the unsaturated hydrocarbons are applicable.

As the hydrocarbons, specifically, there can be cited n-pentane, 2-methylbutane, n-hexane. 2-methylpentane, 2,2-dimethylbutane, 2,3-dimethylbutane, n-heptane, 2-methylhexane, 3-methylhexane, 2,4-dimethylpentane, n-octane, 2-methylheptane, 3-methylheptane, 4-methylheptane-2-dimethylhexane, 2,5-dimethylhexane, 3,3-dimethylhexane, 2-methyl-3-ethylpentane, 3-methyl-3-ethylpentane, 2,3,3-trimethylpentane, 2,3,4-trimethylpentane, 2,2,3-trimethylpentane, 2-methylheptane, 2,2,4-trimethylpentane, n-nonane, 2,2,5-trimethylhexane, n-decane, n-dodecane, cyclopentane, methylcyclopentane, cyclohexane, methylcyclohexane, ethylcyclohexane, bicyclohexane, α-pinene, dipentene, decalin, tetralin, amyl naphthalene, and so on. Among them, n-pentane, cyclopentane, n-hexae, cyclohexane, and n-heptane are more preferable.

As the alcohols which are each the solvent (A), alcohols each having 1 to 16 carbon atoms are preferable. With the alcohols each having 1 to 16 carbon atoms used, a chain structure or a ring structure is applicable, and further saturated alcohols or unsaturated alcohols are applicable.

As the alcohols, specifically, there can be cited methanol, ethanol, 1-propanol, isopropanol, 1-butanol, 2-butanol, 1-methyl-1-propanol, 2-methyl-2-propanol, 1-pentanol, 2-pentanol, 1-ethyl-1-propanol, 2-methyl-1-butanol, 3-methyl-1 butanol, 3-methyl-2-butanol, neopentyl alcohol, 1-hexanol, 2-ethyl-1-pentanol, 4-methyl-2-pentanol, 2-ethyl-1-butanol, 1-heptanal, 2-heptanal, 3-heptanol, 1-octanol, 2-octanol, 2-ethyl-1-hexanol, 1-nonanol, 3,5,5-trimethyl-1-hexanol, 1-decanol, 1-undecanol, 1-dodecanol, allyl alcohol, 2-propyn-1-ol, benzyl alcohol, cyclohexanol, 1-methylcyclohexanol, 2-methylcyclohexanol, 3-methylcyclohexanol, 4-methylcyclohexanol, α-terpineol, 2,6-dimethyl-4-heptanol, nonyl alcohol, tetradecyl alcohol, and so on. Among them, methanol, ethanol, and isopropanol are more preferable.

As the ketones which are each the solvent (A), ketones each having 3 to 9 carbon atoms are preferable, With the ketones each having 3 to 9 carbon atoms used, a chain structure or a ring structure is applicable, and further saturated ketones or unsaturated ketones are applicable.

As the ketones, specifically, there can be cited acetone, methyl ethyl ketone, 2-pentanone, 3-pentanone, 2-hexanone, methyl isobutyl ketone, 2-heptanone, 3-heptanone, 4-heptanone, diisobutyl ketone, mesityl oxide, phorone, 2-octanone, cyclohexanone, methylcyclohexanone, isophorone, 2,4-pentanedione, 2,5-hexanedione, diacetone alcohol, acetophenone, and so on. Among them, acetone and methyl ethyl ketone are more preferable.

As the ethers which are each the solvent (A), ethers each having 2 to 8 carbon atoms are preferable. With the ethers each having 2 to 8 carbon atoms used, a chain structure or a ring structure is applicable, and further saturated ethers or unsaturated ethers are applicable.

As the ethers, specifically, there can be cited diethyl ether, dipropyl ether, diisopropyl ether, dibutyl ether, ethyl vinyl ether, butyl vinyl ether, anisole, phenetole, methyl anisole, furan, methylfuran, and tetrahydrofuran. Among them, diethyl ether, diisopropyl ether, tetrahydrofuran, and so on are more preferable.

As the esters which are each the solvent (A), esters each having 2 to 19 carbon atoms are preferable. With the esters each having 2 to 19 carbon atoms used, a chain structure or a ring structure is applicable, and further saturated esters or unsaturated esters are applicable.

As the esters, specifically, there can be cited methyl formate, ethyl formate, propyl formate, butyl formate, isobutyl formate, pentyl formate, methyl acetate, ethyl acetate, propyl acetate, isopropyl acetate, butyl acetate, isobutyl acetate, sec-butyl acetate, pentyl acetate, methoxybutyl acetate, sec-hexyl acetate, 2-ethylbutyl acetate, 2-ethylhexyl acetate, cyclohexyl acetate, benzyl acetate, methyl propionate, ethyl propionate, butyl propionate, methyl butyrate, ethyl butyrate, butyl butyrate, isobutyl isobutyrate, 2-hydroxy-2-methylpropionic acid ethyl, methyl benzoate, ethyl benzoate, propyl benzoate, butyl benzoate, benzyl benzoate, γ-butyrolactone, diethyl oxalate, dibutyl oxalate, dipentyl oxalate, diethyl malonate, dimethyl maleate, diethyl maleate, dibutyl maleate, dibutyl tartrate, tributyl citrate, dibutyl sebacate, dimethyl phthalate, diethyl phthalate, dibutyl phthalate, and so on. Among them, and methyl acetate and ethyl acetate are more preferable.

As the chlorocarbons which are each the solvent (A), chlorocarbons each having 1 to 3 carbon atoms are preferable. With the chlorocarbons each having 1 to 3 carbon atoms used, a chain structure or a ring structure is applicable, and further saturated chlorocarbons or unsaturated chlorocarbons are applicable.

As the chlorocarbons, specifically, there can be cited methylene chloride, 1,1-dichloroethane, 1,2-dichloroethane, 1,1,2-trichloroethane, 1,1,1,2-tetrachloroethane, 1,1,2,2-tetrachloroethane, pentachloroethane, 1,1-dichloroethylene, cis-1,2-dichloroethylene, trans-1,2-dichloroethylene, trichloroethylene, tetrachloroethylene, 1,2-dichloropropane, and so on. Among them, methylene chloride, trans-1,2-dichloroethylene, and trichloroethylene are more preferable.

As the HFCs which are each the solvent (A), chain or cyclic HFCs each having 4 to 8 carbon atoms are preferable, and solvents included in HFCs in each of which the number of fluorine atoms in one molecule is equal to or more than the number of hydrogen atoms therein are more preferable.

As the HFCs, specifically, there can be cited 1,1,1,3,3-pentafluorobutane, 1,1,1,2,3,4,5,5,5-decafluoropentane, 1,1,2,2,3,3,4-heptafluorocyclopentane, 1,1,1,2,3,3,4,4-nonafluorohexane, 1,1,1,2,2,3,3,4,4,5,5,6,6-tridecafluorohexane, 1,1,1,2,3,3,4,4,5,5,6,6-tridecafluorooctane, and so on. Among them, 1,1,1,2,2,3,4,5,5,5-decafluoropane, 1,1,1,2,2,3,3,4,4-nonafluorohexane, and 1,1,1,2,2,3,3,4,4,5,6,6-tridecafluorohexane are further preferable.

As the HFEs which are each the solvent (A), for example, there can be cited (perfluorobutoxy)methane, (perfluorobutoxy)ethane, 1,1,2-tetrafluoro-1-(2,2,2-trifluoroethoxy)ethane, and so on. Among them, (perfluorobutoxy)methane and 1,1,2,2-tetrafluoro-1-(2,2,2-trifluoroethoxy)ethane are preferable.

As the HCFOs which are each the solvent (A), there can be cited an E-isomer and a Z-isomer of 1-chloro-3,3,3-trifluoro-1-propene, 1,1-dichloro-3,3,3-trifluoro-1-propene, and an E-isomer and a Z-isomer of 1,2-dichloro-3,3,3-trifluoro-1-propene. Among them, the Z-isomer of 1-chloro-3,3,3-trifluoro-1-propene is preferable.

As the CFOs which are each the solvent (A), 1,1-dichloro-2,3,3,3-tetrafluoro-1-propene can be cited.

The solvent (A) is preferably a solvent having no flash point. As the solvent (A) having no flash point, there can be cited the HFCs such as 1,1,1,2,2,3,4,5,5,5-decafluoropentane, 1,1,1,2,2,3,3,4,4-nonafluorohexane, and 1,1,1,2,2,3,3,4,4,5,5,6,6-tridecafluorohexane, the HFEs such as (perfluorobutoxy)methane and 1,1,2,2-tetrafluoro-1-(2,2,2-trifluoroethoxy)ethane, the HCFOs such as an E-isomer and a Z-isomer of 1-Chloro-3,3,3-trifluoro-1-propene, 1,1-dichloro-3,3,3-trifluoro-1-propene, and an E-isomer and a Z-isomer of 1,2-dichloro-3,3,3-trifluoro-1-propene, and the CFOs such as 1,1-dichloro-2,3,3,3-tetrafluoro-1-propene. Even when a solvent having a flash point is used as the solvent (A), it is preferably mixed with HCFO-1233yd and used in a range of having no flash point as the solvent composition of this embodiment.

Further, when HCFO-1233yd and the solvent (A) form azeotropic composition, use in the azeotropic composition is also possible.

When the solvent composition of this embodiment contains the solvent (A), in a content of the solvent (A) in the solvent composition of this embodiment, the solvent (A) is preferably 0.1 to 50 parts by mass, more preferably 0.5 to 20 parts by mass, and further preferably 1 to 10 parts by mass with respect to a total amount of 100 parts by mass of HCFO-1233yd and the solvent (A).

As long as the content of the solvent (A) is equal to or more than the above-described lower limit value, an effect due to the solvent (A) is sufficiently obtained. As long as the content of the solvent (A) is equal to or less than the above-described upper limit value, the excellent drying property which HCFO-1233yd has is not impaired.

The above-explained solvent composition of this embodiment is a stable solvent composition which is excellent in solubility of various organic substances and has no adverse effect on a global environment, and is stabilized not to decompose.

The solvent composition of this embodiment can be used with respect to contact objects with materials in a wide range of metal, plastic, elastomer, glass, ceramic, and so on.

The solvent composition of this embodiment is suitable as a cleaning solvent for cleaning an article to be cleaned, a coating solvent for dissolving a nonvolatile solute and coating it on an article to be coated, a heat transfer fluid for heat cycle system to be used for heating or cooling an article, and the like in particular.

<Cleaning Method>

The cleaning method of the article to be cleaned using the solvent composition of this embodiment is not particularly limited except to remove dirt adhering to an article by using the solvent composition of this embodiment and bringing the solvent composition of this embodiment into contact with a surface of the article to become the article to be cleaned. For example, it is sufficient to employ manual cleaning, immersion cleaning, spray cleaning, immersion-oscillation cleaning, immersion ultrasonic cleaning, steam cleaning, methods by combining these, and the like. Also in a cleaning apparatus, cleaning conditions, and the like, the publicly known ones can be appropriately selected, and repeated use is possible for a long period without decomposition.

As materials of articles to which this solvent composition is applicable, there can be cited metal, resin, rubber, fiber, glass, ceramics, and composite materials of these. As the composite materials, a stack of metal and resin, and the like can be cited.

In exemplifying a cleaning use using the solvent composition of this embodiment, cleaning and removal of flux, a machining oil, wax, a release agent, dust, and the like adhering to various objects to be cleaned can be cited, Here, as more specific examples of the objects to be cleaned, there can be cited fiber products, medical appliances, electric equipment, precision instruments, optical articles, their parts, and the like. As specific examples of the electric equipment, the precision instruments, the optical articles, and their parts, there can be cited an IC, a capacitor, a printed-circuit board, a micromotor, a relay, a bearing, an optical lens, a glass substrate, and the like. Further, for example, a cleaning apparatus and a cleaning method indicated in International Publication No. 2008/149907 can be cited.

When cleaning is performed in the cleaning apparatus described in International Publication No. 2008/149907 by using the solvent composition of this embodiment, a temperature of the solvent composition of this embodiment in a first immersion tank is preferably set to 25° C. or more and less than the boiling point of the solvent composition. As long as the temperature is in the above-described range, it is possible to easily perform the degreasing cleaning of a machining oil or the like, and a cleaning effect by an ultrasonic wave is high. Further, a temperature of the solvent composition of this embodiment in a second immersion tank is preferably set to 10 to 45° C. As long as the temperature is in the above-described range, a difference between a temperature of the article and a temperature of steam of the solvent can be obtained sufficiently in a steam cleaning step, and therefore a sufficient amount of the solvent can be condensed on an article surface for steam cleaning, thereby resulting in a high rinsing effect. In addition, the temperature of the solvent composition of this embodiment in the first immersion tank is preferably higher than the temperature of the solvent composition in the second immersion tank in terms of detergency.

<Dry Cleaning Method>

The solvent composition of this embodiment is suitable as a cleaning solvent for clothing, namely, a dry cleaning solvent.

There can be cited cleaning and removal of dirt adhering to clothing such as a shirt, a sweater, a jacket, a skirt, trousers, a windbreaker, gloves, a muffler, and a stole, as a dry cleaning application using the solvent composition of this embodiment.

Moreover, the solvent composition of this embodiment is applicable to dry cleaning of the clothing made of fibers such as cotton, hemp, wool, rayon, polyester, acrylic, and nylon.

Further, it is found that since HCFO-1233yd included in the solvent composition of this embodiment includes a chlorine atom in its molecule, it has high solubility of the dirt and has cleaning power nearly equal to that of HCFCs such as HCFC-225 having a wide range of solvency, with respect to oil and fat dirt.

Moreover, in order to use the solvent composition of this embodiment as the dry cleaning solvent, it is possible to compound soap in order to enhance the ability to remove water-soluble dirt such as sweat or mud. The soap indicates a surfactant to be used for the dry cleaning, and cationic, nonionic, anionic, and ampholytic surfactants are preferably used. It is found that since HCFO-1233yd has a chlorine atom in its molecule, it has a wide range of solubility to various organic compounds, and it is not required to optimize the soap depending on the solvent as HFEs and HFCs are required, which allows use of various soaps. Hence, the solvent composition of this embodiment can include at least one type of the surfactant selected from a group consisting of the cationic, nonionic, anionic, and ampholytic surfactants.

As a specific example of the soaps, there can be cited a quaternary ammonium salt such as dodecyldimethylammonium chloride or trimethylammonium chloride as the cationic surfactant. There can be cited a surfactant such as polyoxyalkylene nonylphenyl ether, polyoxyalkylene alkyl ether, fatty acid alkanolamide, glycerin fatty acid ester, sorbitan fatty acid ester, sucrose fatty ester, propylene glycol fatty acid ester, or phosphoric acid and fatty acid ester as the nonionic surfactant. There can be cited an alkyl sulfate ester salt such as a polyoxyethylene alkyl sulfate ester salt, a carboxy late salt such as a fatty acid salt (soap), or a sulfonate such as an α-olefin sulfonate or a lauryl sulfate as the anionic surfactant. There can be cited a betaine compound such as alkylbetaine as the ampholytic surfactant.

A content proportion of the soap in the dry cleaning solvent composition is 0.01 to 10 mass %, preferably 0.1 to 5 mass %, and further preferably 0.2 to 2 mass %.

<Coating Solvent Uses>

Further, when the solvent composition of this embodiment is used as a solvent by which a nonvolatile solute component is coated on an article surface, for example, the solvent composition is set to be a solution obtained by dissolving a solute component in the solvent composition of this embodiment, the solution is coated on an article to be coated, and the solvent composition is evaporated to form a nonvolatile component coating film on the above-described article to be coated.

As the nonvolatile component to be mentioned here, there can be cited a lubricant for imparting lubricity to an article, an antirust for imparting an anti-rust effect to metal parts, a moisture-proof coating agent for imparting water repellency to an article, a fingerprint preventing agent for imparting antifouling ability to an article, and the like.

A lubricant can also be dissolved in the solvent composition of this embodiment to be a lubricant solution.

The lubricant means the one which is used for reducing friction on a contact surface and preventing generation of heat and abrasion damage when two members move in a state in which their surfaces are brought into contact with each other. The lubricant may be any form of liquid (oil), semisolid (grease), and solid.

As the lubricant, in terms of excellent solubility to HCFO-1233yd, a fluorine-based lubricant or a silicone-based lubricant is preferable. Note that the fluorine-based lubricant means a lubricant having a fluorine atom in a molecule. Further, the silicone-based lubricant means a lubricant including silicone.

The lubricant included in the above-described lubricant solution may be one type or two or more types. Each of the fluorine-based lubricant and the silicone-based lubricant may be used alone, or they may be used in combination.

As the fluorine-based lubricant, there can be cited a fluorine oil, fluorine grease, or a fluorine-based solid lubricant such as resin powder of polytetrafluoroethylene. As the fluorine oil, a low polymer of perfluoropolyether or chlorotrifluoroethylene is preferable. For example, there can be cited product names "Krytox (registered trademark) GPL102" (manufactured by Du Pont Co., Ltd.), "DAIFLOIL #1", "DAIFLOIL #3", "DAIFLOIL #10", "DAIFLOIL, #20" "DAIFLOIL #50", "DAIFLOIL #100", "DEMNUM S-65" (these are manufactured by Daikin Industries, Ltd.), and the like. As the fluorine grease, the one in which the fluorine oil such as the low polymer of perfluoropolyether or chlorotrifluoroethylene is used as a base oil and powder of polytetrafluoroethylene or other thickeners are compounded is preferable. For example, there can be cited product names "Krytox (registered trademark) grease 240AC" (manufactured by Du Pont Co., Ltd.), "DAIFLOIL grease DG-203", "DEMNUM L65", "DEMNUM L100", "DEMNUM L200", (these are manufactured by Daikin, Ltd.), "Sumitec F936" (manufactured by SUMICO LUBRICANT CO., LID.), "Molykote (registered trademark) HP-300", "Molykote (registered trademark) HP-500", "Molykote (registered trademark) HP-870", "Molykote (registered trademark) 6169" (these are manufactured by Dow Corning Toray Co., Ltd.), and the like.

As the silicone-based lubricant, a silicone oil or silicone grease can be cited. As the silicone oils, a dimethyl silicone, a methyl hydrogen silicone, a methyl phenyl silicone, a cyclic dimethyl silicone, and a modified silicone oil in which an organic group has been introduced into a side chain or a terminal are preferable. For example, there can be cited product names "Shin-Etsu Silicone KF-96", "Shin-Etsu Silicone KF-965", "Shin-Etsu Silicone KF-968", "Shin-Etsu Silicone KF-99", "Shin-Etsu Silicone KF-50", "Shin-Etsu Silicone KF-54", "Shin-Etsu Silicone HIVAC F-4", "Shin-Etsu Silicone HIVAC F-5", "Shin-Etsu Silicone KF-56A", "Shin-Etsu Silicone KF-995" (these are manufactured by Shin-Etsu Chemical Co., Ltd.), "SH200" (manufactured by Dow Corning Toray Co., Ltd.), and the like. As the silicone grease, products in which the various silicone oils cited above are used as a base oil and a thickener such as metal soap or various additives are compounded are preferable. For example, there can be cited product names "Shin-Etsu Silicone G-30 Series", "Shin-Etsu Silicone G-40 Series", "Shin-Etsu Silicone FG-720 Series", "Shin-Etsu Silicone G-411", "Shin-Etsu Silicone G-501", "Shin-Etsu Silicone G-6500", "Shin-Etsu. Silicone G-330", "Shin-Etsu Silicone G-340", "Shin-Etsu Silicone G-350", "Shin-Etsu Silicone G-630" (these are manufactured by Shin-Etsu Chemical Co., Ltd.), "Molykote (registered trademark) SH33L", "Molykote (registered trademark) 41", "Molykote (registered trademark) 44", "Molykote (registered trademark) 822M", "Molykote (registered trademark) 111", "Molykote (registered trademark) grease for high vacuum", "Molykote (registered trademark) heat diffusion compound" (these are manufactured by Dow Corning Toray Co., Ltd.), and the like.

Further, as the one which can be exemplified both as the fluorine-based lubricant and as the silicone-based lubricant, there can be cited a fluorosilicone oil which is a modified silicone oil in which a fluoroalkyl group has been substituted for a terminal or a side chain. For example, there can be cited product names "Unidyne (registered name) TG-5601" (manufactured by Daikin Industries, Ltd.), "Molykote (registered trademark) 3451", "Molykote (registered trademark) 3452", (these are manufactured by Dow Corning Toray Co., Ltd.), "Shin-Etsu Silicone FL-5", "Shin-Etsu Silicone X-22-821", "Shin-Etsu Silicone X-22-822", "Shin-Etsu Silicone FL-100" (these are manufactured by Shin-Etsu Chemical Co., Ltd.), and the like.

These lubricant solutions can be used for industrial equipment, tray parts for a CD and a DVD in a personal computer and an audiovisual apparatus, household appliances and office equipment such as a printer, a copier, and a flux device, and the like for which the fluorine-based lubricant is used. Further, they can be used for a needle and a cylinder of a syringe, medical tube parts, and the like for which the silicone-based lubricant is used.

A content of the lubricant in the above-described lubricant solution (100 mass %) is preferably 0.01 to 50 mass %, more preferably 0.05 to 30 mass %, and further preferably 0.1 to 20 mass %. As long as the content of the lubricant is in the above-described range, a film thickness of a coating film when the lubricant solution is coated and a thickness of a lubricant coating film after drying are easily regulated in a proper range. Similarly, a content of an antirust in an antirust solution is also preferably in the same range as the above-described one.

As a coating method of the lubricant solution, for example, there can be cited coating by using a brush, coating by spraying, coating by immersing the articles in the lubricant solution, a coating method of bringing the lubricant solution into contact with an inner wall of a tube or a needle by pumping up the lubricant solution.

The antirust in this embodiment means a substance which prevents rust of metal materials by covering a surface of metals which are easily oxidized by oxygen in the air to generate rust and blocking oxygen from the metal surface. As the antirusts, there can be cited a mineral oil, and synthetic oils such as polyol esters, polyalkylene glycols, and polyvinyl ethers.

A coating method of the antirust is similar to that of the lubricant, and there can be cited coating by using a brush, coating by spraying, coating by immersing the articles in the antirust solution, or the like.

Other than the above, the moisture-proof coating agent and the fingerprint preventing agent for imparting a moisture-proof property and an antifouling property to plastic, rubber, metal, glass, and a mounted circuit board can also be coated on the article surface in a similar method. As product examples of the moisture-proof coating agent, there can be cited TOPAS 5013, TOPAS 6013, TOPAS 8007 (products manufactured by Polyplastics Co., Ltd.), ZEONOR 10208, ZEONOR 1060R (products manufactured by Zeon Corporation), Apel 6011T, Apel 8008T, (products manufactured by Mitsui Chemicals, Inc.), SFE-DP02H, SNF-DP20H (products manufactured by AGC SEIMI CHEMICAL CO., LTD.). As product examples of the antifouling coating agent such as a fingerprint preventing agent, there can be cited OPTOOL DSX, OPTOOL DAC (products manufactured by Daikin Industries, Ltd.), Fluoro Surf FG-500 (a product manufactured by Fluoro Technology Co., Ltd.), SR-4000A (a product manufactured by AGC SEIMI CHEMICAL CO., LTD.), and the like.

As the objects to be coated on which the lubricant and the antirust, the moisture-proof coating agent, and the fingerprint preventing agent are coated, the objects to be coated made of various materials such as metal, plastic, elastomer, glass, and ceramics can be employed.

Either in a state of the solvent composition of this embodiment before dissolving these lubricant and antirust, moisture-proof coating agent, fingerprint preventing agent, and the like, or in a state of the above-described solution, the use is possible without decomposition in storage or in use. The above-explained solvent composition of this embodiment has a short lifetime in the atmosphere and is excellent in solubility, has no adverse effect on a global environment, and can be used in a stable state without decomposing, <Heat Transfer Fluid Uses>

In heat transfer fluid uses of this embodiment, the solvent composition of this embodiment can be used as a working fluid (heat transfer fluid) for a heat cycle system. This makes it possible to heat or cool substances.

As the heat cycle systems, there can be cited a Rankine cycle system, a heat pump cycle system, a refrigeration cycle system, a heat transport system, a secondary refrigerant cooling system, and the like.

Hereinafter, as one example of the heat cycle system, the refrigeration cycle system will be explained.

The refrigeration cycle system is a system in which the working fluid removes heat energy from a load fluid in an evaporator, thereby cooling the load fluid and cooling it to lower temperature. The refrigeration cycle system is a system constituted of a compressor which compresses a working fluid vapor A to make it into a working fluid vapor B at high temperature and high pressure, a condenser Which cools and liquefies the compressed working fluid vapor B to make it into a working fluid C at low temperature and high pressure, an expansion valve which expands the working fluid C emitted from the condenser to make it into a working fluid D at low temperature and low pressure, an evaporator which heats the working fluid D emitted from the expansion valve to make it into the working fluid vapor A at high temperature and low pressure, a pump which supplies a load fluid E to the evaporator, and a pump which supplies a fluid F to the condenser.

Moreover, a lubricating oil can be used for the working fluid of this embodiment. For the lubricating oil, a publicly known lubricating oil to be used for the heat cycle system is used. As the lubricating oils, there can be cited an oxygenated synthetic oil (ester-based lubricating oil, ether-based lubricating oil, or the like), a fluorine-based lubricating oil, a mineral oil, a hydrocarbon-based synthetic oil, and the like.

Moreover, the working fluid of this embodiment is also applicable to a secondary circulation cooling system.

The secondary circulation cooling system is a system having a primary cooling device which cools a primary refrigerant constituted of ammonia or a hydrocarbon refrigerant, a secondary circulation cooling device which cools an article to be cooled by circulating a secondary refrigerant for secondary circulation cooling system (hereinafter, referred to as "secondary refrigerant"), and a heat exchanger which exchanges heat between the primary refrigerant and the secondary refrigerant and cools the secondary refrigerant. This secondary circulation cooling system allows cooling of the article to be cooled. The working fluid of this embodiment is suitable for use as the secondary refrigerant.

EXAMPLES

Reference Example: Production of HCFO-1233yd 2000 g of HCFO-244ca was used as a raw material, 19.9 g of tetra-n-butyl ammonium chloride was put in, a reaction temperature was kept at 50° C., and 2792 g of a 40 mass % aqueous potassium hydroxide solution was dropped over 30 minutes. Thereafter, a reaction was continued for 52 hours, and an organic layer was recovered. The recovered organic layer was purified, resulting in obtaining 1520 g of purity 99.9 mass % HCFO-1233yd(Z) and 140 g of purity 99.9 mass % HCFO-1233yd(E). This reaction was repeatedly performed to produce a required amount of HCFO-1233yd (Z) or HCFO-1233yd(E).

Further, HCFO-1233yd(Z) and HCFO-1233yd(E) obtained by a similar reaction were separated as a mixture to produce an isomer mixture of HCFO-1233yd(Z) and HCFO-1233yd(E) as well. The isomer mixture obtained at this time was 95 mass % of HCFO-1233yd(Z) and 5 mass % of HCFO-1233yd(E).

Example: Production of Solvent Composition

To purity 99.9 mass % HCFO-1233yd(Z) or HCFO-1233yd(E), or the isomer mixture of HCFO-1233yd, stabilizers were each added so as to become a predetermined concentration as presented in Tables 1 to 3, and 100 g each of solvent compositions was prepared. Note that in Tables 3 to 6, the isomer mixture of HCFO-1233yd obtained in the above-described reference example was simply indicated as "HCFO-1233yd";

Test Example 1: Stability Test

The obtained solvent compositions were retained at 50° C. for three days. Tables 1 to 3 present the results of measuring chlorine ion concentrations immediately after the preparation and after the retention. Any of indices of the evaluation is a chlorine ion concentration.

<Index of Evaluation>

"A (excellent): less than 10 mass ppm"

"B (good): 10 mass ppm or more and less than 50 mass ppm"

"C (slightly poor): 50 mass ppm or more and less than 100 mass ppm"

"D (poor): 100 mass ppm or more"

In the chlorine ion concentration measurement, 40 g of each of the solvent compositions and 40 g of ion-exchange water were put in a 200 mL-capacity separatory funnel, shaken for one minute, and thereafter left still, and an upper-layer aqueous phase obtained by a two-layer separation was separately collected, and the chlorine ion concentration of the aqueous phase was measured by an ion chromatograph (model number: ICS-1000, manufactured by Dionex Corporation, anion analysis column: Dionex Ionpac AS12A).

Examples 3 to 82 presented in Tables 1 to 3 indicate Examples, and Examples 1 and 2 indicate Comparative examples. The present Examples indicated that any of the solvent compositions of this embodiment had high stability.

Furthermore, a drying property was evaluated based on how traces remain when one drop of each of the solvent compositions in Examples 1 to 82 was dropped by using a Pasteur pipette and volatilized on a mirror-finished SUS plate under room temperate e.

<Index of Evaluation>

"A (excellent): no trace remains due to complete volatilization of the solvent composition"

"B (good): no trace remains due to considerable volatilization of the solvent composition"

"C (possible): a slight residue is recognized, but there is no practical problem"

"D (poor): a visible residue is recognized"

Examples 3 to 43, 49 to 71, and 78 to 82 in each of which the solvent composition including a stabilizer whose boiling point was 30 to 120° C. was used indicated that the solvent composition volatilized with no trace remaining. On the other hand, Examples 44 to 48, and 72 to 77 in each of which a stabilizer whose boiling point was higher than 120° C. was included indicated a degree to which a slight residue was recognized after the volatilization but there was no practical problem.

TABLE 1

| Example number | Substance | Stabilizer | Concentration [mass %] | Stability Before test | Stability After test | Drying property |
|---|---|---|---|---|---|---|
| 1 | HCFO-1233yd(Z) | Absence | — | A | D | A |
| 2 | HCFO-1233yd(E) | Absence | — | A | D | A |
| 3 | HCFO-1233yd(Z) | Methanol | 1 | A | B | A |
| 4 | HCFO-1233yd(Z) | Methanol | 0.1 | A | A | A |
| 5 | HCFO-1233yd(Z) | Methanol | 0.001 | A | A | A |
| 6 | HCFO-1233yd(Z) | Methanol | 0.0001 | A | B | A |
| 7 | HCFO-1233yd(Z) | Ethanol | 0.01 | A | A | A |
| 8 | HCFO-1233yd(Z) | Isopropanol | 0.01 | A | A | A |

TABLE 1-continued

| Example number | Substance | Stabilizer | Concentration [mass %] | Stability Before test | Stability After test | Drying property |
|---|---|---|---|---|---|---|
| 9 | HCFO-1233yd(Z) | 2-propyn-1-ol | 0.01 | A | A | A |
| 10 | HCFO-1233yd(Z) | 1,2-butylene oxide | 0.1 | A | A | A |
| 11 | HCFO-1233yd(Z) | Tetrahydrofuran | 0.1 | A | A | A |
| 12 | HCFO-1233yd(Z) | 1,4-dioxane | 0.1 | A | A | A |
| 13 | HCFO-1233yd(Z) | 2-methyl-2-butene | 1 | A | B | A |
| 14 | HCFO-1233yd(Z) | 2-methyl-2-butene | 0.1 | A | A | A |
| 15 | HCFO-1233yd(Z) | 2-methyl-2-butene | 0.001 | A | A | A |
| 16 | HCFO-1233yd(Z) | 2-methyl-2-butene | 0.0001 | A | B | A |
| 17 | HCFO-1233yd(Z) | 2-methyl-1-pentene | 0.1 | A | A | A |
| 18 | HCFO-1233yd(Z) | 2-methyl-2-pentene | 1 | A | B | A |
| 19 | HCFO-1233yd(Z) | 2-methyl-2-pentene | 0.1 | A | A | A |
| 20 | HCFO-1233yd(E) | 2-methyl-2-pentene | 0.1 | A | A | A |
| 21 | HCFO-1233yd(Z) | 2-methyl-2-pentene | 0.001 | A | A | A |
| 22 | HCFO-1233yd(Z) | 2-methyl-2-pentene | 0.0001 | A | B | A |
| 23 | HCFO-1233yd(Z) | 3-ethyl-2-butene | 0.1 | A | A | A |
| 24 | HCFO-1233yd(Z) | 2,3-dimethyl-2-butene | 0.1 | A | A | A |
| 25 | HCFO-1233yd(Z) | 2,4,4-trimethyl-1-pentene | 0.1 | A | A | A |
| 26 | HCFO-1233yd(Z) | 2,4,4-trimethyl-2-pentene | 1 | A | B | A |
| 27 | HCFO-1233yd(Z) | 2,4,4-trimethyl-2-pentene | 0.1 | A | A | A |
| 28 | HCFO-1233yd(E) | 2,4,4-trimethyl-2-pentene | 0.1 | A | A | A |
| 29 | HCFO-1233yd(Z) | 2,4,4-trimethyl-2-pentene | 0.001 | A | A | A |
| 30 | HCFO-1233yd(Z) | 2,4,4-trimethyl-2-pentene | 0.0001 | A | B | A |
| 31 | HCFO-1233yd(Z) | n-heptane | 1 | A | B | A |
| 32 | HCFO-1233yd(Z) | n-heptane | 0.1 | A | A | A |
| 33 | HCFO-1233yd(Z) | n-heptane | 0.001 | A | A | A |
| 34 | HCFO-1233yd(Z) | n-heptane | 0.0001 | A | B | A |
| 35 | HCFO-1233yd(Z) | n-propylamine | 0.01 | A | A | A |
| 36 | HCFO-1233yd(Z) | Diisopropylamine | 0.01 | A | A | A |
| 37 | HCFO-1233yd(Z) | N-methylmorpholine | 0.01 | A | A | A |
| 38 | HCFO-1233yd(Z) | N-methylmorpholine | 0.001 | A | A | A |
| 39 | HCFO-1233yd(E) | N-methylmorpholine | 0.01 | A | A | A |
| 40 | HCFO-1233yd(Z) | N-methylpyrrole | 0.1 | A | A | A |
| 41 | HCFO-1233yd(Z) | N-methylpyrrole | 0.001 | A | A | A |
| 42 | HCFO-1233yd(Z) | N-methylpyrrole | 0.0001 | A | B | A |
| 43 | HCFO-1233yd(E) | N-methylpyrrole | 0.1 | A | A | A |
| 44 | HCFO-1233yd(Z) | 2,6-di-tert-butyl-4-methylphenol | 0.1 | A | A | C |
| 45 | HCFO-1233yd(Z) | 2,6-di-tert-butyl-4-methylphenol | 0.001 | A | A | C |
| 46 | HCFO-1233yd(E) | 2,6-di-tert-butyl-4-methylphenol | 0.1 | A | A | C |
| 47 | HCFO-1233yd(Z) | p-methoxyphenol | 0.1 | A | A | C |
| 48 | HCFO-1233yd(E) | p-methoxyphenol | 0.1 | A | A | C |

TABLE 2

| Example number | Substance | Stabilizer | Concentration [mass %] | Stability Before test | Stability After test | Drying property |
|---|---|---|---|---|---|---|
| 49 | HCFO-1233yd(Z) | 2-methyl-2-butene<br>Methanol | 1<br>1 | A | B | A |
| 50 | HCFO-1233yd(Z) | 2-methyl-2-butene<br>Methanol | 0.1<br>0.1 | A | A | A |
| 51 | HCFO-1233yd(Z) | 2-methyl-2-butene<br>Methanol | 0.001<br>0.001 | A | A | A |
| 52 | HCFO-1233yd(Z) | 2-methyl-2-pentene<br>Methanol | 0.1<br>0.1 | A | A | A |
| 53 | HCFO-1233yd(Z) | 2-methyl-2-pentene<br>Methanol | 0.001<br>0.001 | A | A | A |
| 54 | HCFO-1233yd(E) | 2-methyl-2-pentene<br>Methanol | 0.1<br>0.1 | A | A | A |
| 55 | HCFO-1233yd(Z) | 2-methyl-2-pentene<br>2-propyn-1-ol | 0.1<br>0.01 | A | A | A |
| 56 | HCFO-1233yd(Z) | 2-methyl-1-pentene<br>2-propyn-1-ol | 0.1<br>0.01 | A | A | A |
| 57 | HCFO-1233yd(Z) | 2-methyl-2-pentene<br>2-propyn-1-ol | 0.01<br>0.1 | A | A | A |
| 58 | HCFO-1233yd(Z) | 2,4,4-trimethyl-2-pentene<br>Methanol | 0.1<br>0.01 | A | A | A |
| 59 | HCFO-1233yd(Z) | 2,4,4-trimethyl-2-pentene<br>Methanol | 0.01<br>0.1 | A | A | A |
| 60 | HCFO-1233yd(Z) | 2,4,4-trimethyl-2-pentene<br>Methanol | 0.01<br>0.01 | A | A | A |

TABLE 2-continued

| Example number | Substance | Stabilizer | Concentration [mass %] | Stability Before test | Stability After test | Drying property |
|---|---|---|---|---|---|---|
| 61 | HCFO-1233yd(E) | 2,4,4-trimethyl-2-pentene<br>Methanol | 0.01<br>0.01 | A | A | A |
| 62 | HCFO-1233yd(Z) | 2,4,4-trimethyl-2-pentene<br>2-propyn-1-ol | 0.01<br>0.01 | A | A | A |
| 63 | HCFO-1233yd(Z) | 2,4,4-trimethyl-1-pentene<br>2-propyn-1-ol | 0.01<br>0.01 | A | A | A |
| 64 | HCFO-1233yd(Z) | 2-methyl-2-butene<br>Methanol<br>N-methylmorpholine | 0.01<br>0.01<br>0.001 | A | A | A |
| 65 | HCFO-1233yd(Z) | 2-methyl-2-pentene<br>2-propyn-1-ol<br>N-methylmorpholine | 0.01<br>0.01<br>0.001 | A | A | A |
| 66 | HCFO-1233yd(Z) | 2-methyl-2-pentene<br>2-propyn-1-ol<br>N-methylmorpholine | 0.1<br>0.01<br>0.001 | A | A | A |
| 67 | HCFO-1233yd(Z) | 2,4,4-trimethyl-2-pentene<br>Methanol<br>N-methylmorpholine | 0.01<br>0.01<br>0.001 | A | A | A |
| 68 | HCFO-1233yd(E) | 2,4,4-trimethyl-2-pentene<br>Methanol<br>N-methylmorpholine | 0.01<br>0.01<br>0.001 | A | A | A |
| 69 | HCFO-1233yd(Z) | 2-methyl-2-butene<br>Methanol<br>N-methylpyrrole | 0.01<br>0.01<br>0.01 | A | A | A |
| 70 | HCFO-1233yd(Z) | 2-methyl-2-pentene<br>2-propyn-1-ol<br>N-methylpyrrole | 0.01<br>0.01<br>0.01 | A | A | A |
| 71 | HCFO-1233yd(Z) | 2,4,4-trimethyl-2-pentene<br>2-propyn-1-ol<br>N-methylpyrrole | 0.01<br>0.01<br>0.01 | A | A | A |

TABLE 3

| Example number | Substance | Stabilizer | Concentration [mass %] | Stability Before test | Stability After test | Drying property |
|---|---|---|---|---|---|---|
| 72 | HCFO-1233yd(Z) | 2-methyl-2-butene<br>Methanol<br>2,6-di-tert-butyl-4-methylphenol | 0.1<br>0.1<br>0.001 | A | A | C |
| 73 | HCFO-1233yd(Z) | 2-methyl-2-butene<br>Methanol<br>2,6-di-tert-butyl-4-methylphenol | 0.01<br>0.01<br>0.001 | A | A | C |
| 74 | HCFO-1233yd(Z) | 2-methyl-2-butene<br>Methanol<br>2,6-di-tert-butyl-4-methylphenol | 0.1<br>0.1<br>0.1 | A | A | C |
| 75 | HCFO-1233yd(Z) | 2-methyl-2-pentene<br>2-propyn-1-ol<br>2,6-di-tert-butyl-4-methylphenol | 0.01<br>0.01<br>0.1 | A | A | C |
| 76 | HCFO-1233yd(Z) | 2,4,4-trimethyl-2-pentene<br>Methanol<br>2,6-di-tert-butyl-4-methylphenol | 0.01<br>0.01<br>0.1 | A | A | C |
| 77 | HCFO-1233yd | 2-methyl-2-pentene<br>Methanol<br>2,6-di-tert-butyl-4-methylphenol | 0.01<br>0.1<br>0.1 | A | A | C |
| 78 | HCFO-1233yd | 2-methyl-2-pentene<br>Methanol | 0.05<br>0.01 | A | A | A |
| 79 | HCFO-1233yd | 2-methyl-2-pentene<br>2-propyn-1-ol | 0.05<br>0.01 | A | A | A |
| 80 | HCFO-1233yd | 2,4,4-trimethyl-1-pentene<br>Methanol | 0.1<br>0.01 | A | A | A |
| 81 | HCFO-1233yd | 2,4,4-trimethyl-1-pentene<br>2,4,4-trimethyl-2-pentene<br>2-propyn-1-ol | 0.05<br>0.01<br>0.01 | A | A | A |
| 82 | HCFO-1233yd | 2-methyl-2-pentene<br>N-methylpyrrole | 0.1<br>0.05 | A | A | A |

Test Example 2: Stability Evaluation Test by Accelerated Oxidation Test

Regarding the solvent compositions in Examples 4, 14, 19, 20, 27, 28, 50, 52, 55, 60, 78, and 80 (Examples) and Examples 1 and 2 (Comparative examples) described above, a test for confirming stability in a reflux time of 48 hours was conducted in conformity to an accelerated oxidation test of Japan Industrial Standard JIS K 1508-1982. In 200 mL of each of the solvent compositions, under a condition in which a test piece of carbon steel for machine structural use (S20C) was made to coexist in a gas phase and a liquid phase, while passing oxygen bubbles saturated with moisture, light was irradiated by an electric bulb, and reflux was performed by heat generation of the electric bulb.

Table 4 presents evaluation results of chlorine ion concentrations before and after the test and test piece appearance, Note that the evaluation of the chlorine ion concentrations is as follows.

"A (excellent): less than 10 mass ppm"
"B (good): 10 mass ppm or more and less than 50 ppm"
"C (slightly poor): 50 mass ppm or more and less than 100 ppm"
"D (poor): 100 mass ppm or more"

Further, evaluation criteria of the test piece appearance are as follows.

"A (excellent): there is no change before and after the test"
"B (good): a gloss has been slightly lost, but there is no practical problem"
"C (slightly poor): a surface slightly rusts"
"D (poor): rust is recognized on the whole surface of a surface"

Test Example 3: Evaluation of Cleaning Ability

Regarding a part of the solvent compositions obtained in Examples, each of the following cleaning tests was performed, and Table 5 presented the results.

[Cleaning Test A]

After immersing a test piece (25 mm×30 mm×2 mm) of SUS-304 in a product name "Daphne Magplus HT-10" (manufactured by Idemitsu Kosan Co., Ltd.) which was a cutting oil, the test piece was immersed in 50 mL of the solvent composition in each of the examples for one minute and pulled up, and degrees to which the cutting oil was removed were observed. Evaluation of detergency was performed in accordance with the following criteria.

"A (excellent): the cutting oil is completely removed."
"B (good): the cutting oil is almost removed."
"C (slightly poor): the cutting oil remains in trace amounts."
"D (poor): the cutting oil considerably remains."

[Cleaning Test B]

A test was conducted similarly to the cleaning test A except to use a product name "Daphne Magplus AM20" (manufactured by Idemitsu Kosan Co., Ltd.) as a cutting oil, and detergency was evaluated by the same criteria.

[Cleaning test C]

A test was conducted similarly to the cleaning test A except to use a product name "Daphne Magplus HM25" (manufactured by Idemitsu Kosan Co., Ltd.) as a cutting oil, and detergency was evaluated by the same criteria.

[Cleaning Test D]

A test was conducted similarly to the cleaning test A except to use a product name "G-6318FK" (manufactured

TABLE 4

| Example number | Substance | Stabilizer | Concentration [mass %] | Chlorine ion concentration Before test | Chlorine ion concentration After test | Test piece appearance after test Gas phase | Test piece appearance after test Liquid phase |
|---|---|---|---|---|---|---|---|
| 1 | HCFO-1233yd(Z) | Absence | — | A | D | D | D |
| 2 | HCFO-1233yd(E) | Absence | — | A | D | D | D |
| 4 | HCFO-1233yd(Z) | Methanol | 0.1 | A | B | B | B |
| 14 | HCFO-1233yd(Z) | 2-methyl-2-butene | 0.1 | A | B | B | B |
| 19 | HCFO-1233yd(Z) | 2-methyl-2-pentene | 0.1 | A | A | A | A |
| 20 | HCFO-1233yd(E) | 2-methyl-2-pentene | 0.1 | A | A | A | A |
| 27 | HCFO-1233yd(Z) | 2,4,4-trimethyl-1-pentene | 0.1 | A | A | A | A |
| 28 | HCFO-1233yd(Z) | 2,4,4-trimethyl-2-pentene | 0.1 | A | A | A | A |
| 50 | HCFO-1233yd(Z) | 2-methyl-2-butene Methanol | 0.1 0.1 | A | B | A | A |
| 52 | HCFO-1233yd(Z) | 2-methyl-2-pentene Methanol | 0.1 0.1 | A | A | A | A |
| 55 | HCFO-1233yd(Z) | 2-methyl-2-pentene 2-propyn-1-ol | 0.1 0.01 | A | A | A | A |
| 60 | HCFO-1233yd(Z) | 2,4,4-trimethyl-2-pentene Methanol | 0.01 0.01 | A | A | A | A |
| 78 | HCFO-1233yd | 2-methyl-2-pentene Methanol | 0.05 0.01 | A | A | A | A |
| 80 | HCFO-1233yd | 2,4,4-trimethyl-1-pentene Methanol | 0.1 0.01 | A | A | A | A |

According to the present test results, it became clear that any of the solvent compositions in Examples was more excellent in stability than those in Comparative examples. Moreover, it became clear that the solvent compositions in Examples 19, 20, 27, 28, 52, 55, 60, 78, and 80 were more excellent in stability.

by NIHON KOHSAKUYU CO., LTD.) as a cutting oil, and detergency was evaluated by the same criteria.

As presented in Table 5, it was indicated that in any of the cleaning tests, the solvent compositions of this embodiment were each capable of cleaning and removing the cutting oils sufficiently and each had excellent detergency similarly to those in Examples 1 and 2 to which no stabilizer was added.

"A (excellent): immediately uniformly dissolved to become transparent."

TABLE 5

| Example number | Substance | Stabilizer | Concentration [mass %] | Detergency Test A | Test B | Test C | Test D |
|---|---|---|---|---|---|---|---|
| 1 | HCFO-1233yd(Z) | Absence | — | A | A | A | A |
| 2 | HCFO-1233yd(E) | Absence | — | A | A | A | A |
| 4 | HCFO-1233yd(Z) | Methanol | 0.1 | A | A | A | A |
| 14 | HCFO-1233yd(Z) | 2-methyl-2-butene | 0.1 | A | A | A | A |
| 19 | HCFO-1233yd(Z) | 2-methyl-2-pentene | 0.001 | A | A | A | A |
| 20 | HCFO-1233yd(E) | 2-methyl-2-pentene | 0.1 | A | A | A | A |
| 21 | HCFO-1233yd(Z) | 2-methyl-2-pentene | 0.1 | A | A | A | A |
| 27 | HCFO-1233yd(Z) | 2,4,4-trimethyl-2-pentene | 0.1 | A | A | A | A |
| 28 | HCFO-1233yd(E) | 2,4,4-trimethyl-2-pentene | 0.1 | A | A | A | A |
| 29 | HCFO-1233yd(Z) | 2,4,4-trimethyl-2-pentene | 0.1 | A | A | A | A |
| 50 | HCFO-1233yd(Z) | 2-methyl-2-butene<br>Methanol | 0.01<br>0.01 | A | A | A | A |
| 52 | HCFO-1233yd(Z) | 2-methyl-2-pentene<br>Methanol | 0.01<br>0.001 | A | A | A | A |
| 55 | HCFO-1233yd(Z) | 2-methyl-2-pentene<br>2-propyn-1-ol | 0.01<br>0.01 | A | A | A | A |
| 58 | HCFO-1233yd(Z) | 2,4,4-trimethyl-2-pentene<br>Methanol | 0.01<br>0.01 | A | A | A | A |
| 60 | HCFO-1233yd(Z) | 2,4,4-trimethyl-2-pentene<br>Methanol | 0.01<br>0.001 | A | A | A | A |
| 75 | HCFO-1233yd(Z) | 2-methyl-2-pentene<br>2-propyn-1-ol<br>2,6-di-tert-butyl-4-methylphenol | 0.01<br>0.01<br>0.1 | A | A | A | A |
| 76 | HCFO-1233yd(Z) | 2,4,4-trimethyl-2-pentene<br>Methanol<br>2,6-di-tert-butyl-4-methylphenol | 0.01<br>0.01<br>0.1 | A | A | A | A |
| 78 | HCFO-1233yd | 2-methyl-2-pentene<br>Methanol | 0.05<br>0.01 | A | A | A | A |
| 80 | HCFO-1233yd | 2,4,4-trimethyl-1-pentene<br>Methanol | 0.1<br>0.01 | A | A | A | A |

Test Example 4: Evaluation of Ability as Coating Solvent

A part of the solvent compositions obtained in Examples and a product name "Krytox (registered trademark) GPL102" (manufactured by Du Pont Co., Ltd., fluorine-based oil) which was a fluorine-based lubricant were mixed with each other, and a lubricant solution in which a content of the fluorine-based lubricant was 0.5 mass % was prepared as a coating solvent.

Next, on a surface of an aluminum deposited sheet in which aluminum was deposited on a sheet made of iron, the obtained lubricant solutions were each coated in a thickness of 0.4 mm and air-dried under a condition of 19° C. to 21° C., thereby each forming a lubricant coating film on the aluminum deposited sheet surface. Evaluation of a dissolved state of each of the lubricant solutions and evaluation of the ability as each of the lubricant coating films were performed as follows, and Table 6 presented the results.

[Dissolved State]

A dissolved state of the lubricant solution in each of the examples was visually confirmed 1.5 to be evaluated by the following criteria.

"B (good): if shaken, uniformly dissolved to become transparent."

"C (slightly poor): slightly cloudy."

"D (poor): cloudy or phase-separated."

[Coating Film State]

A state of the lubricant coating film in each of the examples was visually confirmed to be evaluated by the following criteria.

"A (excellent): a uniform coating film is formed."

"B (good): an almost uniform coating film is formed."

"C (slightly poor): nonuniformity is partially seen on the coating film."

"D (poor): nonuniformity is considerably seen on the coating film."

As presented in Table 6, it became clear that in any of the coating tests, the coating solvents of this embodiment were each excellent in solubility of the lubricant and each capable of simply forming a uniform lubricant coating film similarly to those in Examples 1 and 2 each having no stabilizer.

TABLE 6

| Example number | Substance | Stabilizer | Concentration [mass %] | Dissolved state | Coating film state |
|---|---|---|---|---|---|
| 1 | HCFO-1233yd(Z) | Absence | — | A | A |
| 2 | HCFO-1233yd(E) | Absence | — | A | A |
| 4 | HCFO-1233yd(Z) | Methanol | 0.1 | A | A |
| 14 | HCFO-1233yd(Z) | 2-methyl-2-butene | 0.1 | A | A |
| 19 | HCFO-1233yd(Z) | 2-methyl-2-pentene | 0.001 | A | A |

TABLE 6-continued

| Example number | Substance | Stabilizer | Concentration [mass %] | Dissolved state | Coating film state |
|---|---|---|---|---|---|
| 20 | HCFO-1233yd(E) | 2-methyl-2-pentene | 0.1 | A | A |
| 21 | HCFO-1233yd(Z) | 2-methyl-2-pentene | 0.1 | A | A |
| 27 | HCFO-1233yd(Z) | 2,4,4-trimethyl-2-pentene | 0.1 | A | A |
| 28 | HCFO-1233yd(E) | 2,4,4-trimethyl-2-pentene | 0.1 | A | A |
| 29 | HCFO-1233yd(Z) | 2,4,4-trimethyl-2-pentene | 0.1 | A | A |
| 50 | HCFO-1233yd(Z) | 2-methyl-2-butene<br>Methanol | 0.01<br>0.01 | A | A |
| 52 | HCFO-1233yd(Z) | 2-methyl-2-pentene<br>Methanol | 0.01<br>0.001 | A | A |
| 55 | HCFO-1233yd(Z) | 2-methyl-2-pentene<br>2-propyn-1-ol | 0.01<br>0.01 | A | A |
| 58 | HCFO-1233yd(Z) | 2,4,4-trimethyl-2-pentene<br>Methanol | 0.01<br>0.01 | A | A |
| 60 | HCFO-1233yd(Z) | 2,4,4-trimethyl-2-pentene<br>Methanol | 0.01<br>0.001 | A | A |
| 75 | HCFO-1233yd(Z) | 2-methyl-2-pentene<br>2-propyn-1-ol<br>2,6-di-tert-butyl-4-methylphenol | 0.01<br>0.01<br>0.1 | A | A |
| 76 | HCFO-1233yd(Z) | 2,4,4-trimethyl-2-pentene<br>Methanol<br>2,6-di-tert-butyl-4-methylphenol | 0.01<br>0.01<br>0.1 | A | A |
| 78 | HCFO-1233yd | 2-methyl-2-pentene<br>Methanol | 0.05<br>0.01 | A | A |
| 80 | HCFO-1233yd | 2,4,4-trimethyl-1-pentene<br>Methanol | 0.1<br>0.01 | A | A |

Test Example 5: Evaluation of Detergency and Feeling for Clothing

A white cardigan made of wool fabric was cleaned by using the solvent composition of this embodiment to evaluate a state of detergency and feeling as follows.

10 L (15 kg) of the solvent composition in Example 50 was prepared at the beginning. Moreover, 75 g (0.5 mass %) of NF-98 (manufactured by NICCA CHEMICAL CO., LTD.: brand name "NF-98") was added as soap and stirred well, to make a test solvent to be used for a cleaning test.

The above-described cardigan which was worn and became dirty was cut in half, and one of the ones cut in half was used for the cleaning test. For the test cleaning, a dry cleaning tester (brand name: DC-1A, manufactured by DAIEI AGAKU SEMI MFG, CO., LTD.) was used, the above-described test solvent and the article to be cleaned were put in a cleaning tank whose capacity was about 11 L, and cleaning was performed at room temperature for ten minutes. Thereafter, the cleaned cardigan was taken out of the cleaning tank and sufficiently dried, and the cleaning ability and the feeling were evaluated compared with the remaining half cardigan which was not cleaned. As a comparative example, a similar cleaning test was performed on HFC-365mfc and HFE-347pc-f which were conventional cleaning solvents.

As a result, the cardigan cleaned by the test solvent based on the solvent composition in Example 50 had the detergency and the feeling equal to those when it was cleaned by the conventional solvents.

INDUSTRIAL APPLICABILITY

A solvent composition of the present invention is a stable solvent composition which is excellent in solubility of various organic substances and has no adverse effect on a global environment, and is stabilized not to decompose. This solvent composition is useful for a wide range of industrial uses such as cleaning and coating uses and can be used for articles of various materials such as metal, plastic, and elastomer without giving adverse effects.

What is claimed is:

1. A solvent composition comprising:
   1-chloro-2,3,3-trifluoro-1-propene; and
   a stabilizer comprising an unsaturated hydrocarbon comprising 1-pentene, 2-pentene, 2-methyl-1-butene, 3-methyl-1-butene, 2-methyl-2-butene, 1-hexene, 2-hexene, 3-hexene, 2-methyl-1-pentene, 3-methyl-1-pentene, 4-methyl-1-pentene, 2-ethyl-1-butene, 3-ethyl-1-butene, 3-ethyl-2-butene, 2-methyl-2-pentene, 3-methyl-2-pentene, 4-methyl-2-pentene, 2,3-dimethyl-2-butene, 1-heptene, 2-heptene, 3-heptene, 4-heptene, 3-ethyl-2-pentene, 1-octene, 2,4,4-trimethyl-1-pentene, 2,4,4-trimethyl-2-pentene, 1-nonene, butadiene, isoprene, hexadiene, heptadiene, octadiene, cyclohexene, cyclohexadiene, cycloheptene, cycloheptadiene, cyclooctene and/or cyclooctadiene.

2. The solvent composition of claim 1, wherein a content of the stabilizer is from 1 mass ppm to 10 mass % in the solvent composition (100 mass %).

3. The solvent composition of claim 1, wherein a content of 1-chloro-2,3,3-trifluoro-1-propene is 80 mass % or more in the solvent composition (100 mass %).

4. The solvent composition of claim 1,
   wherein the 1-chloro-2,3,3-trifluoro-1-propene is a mixture of a Z-isomer of 1-chloro-2,3,3-trifluoro-1-propene and an E-isomer of 1-chloro-2,3,3-trifluoro-1-propene, and
   wherein a content proportion of the Z-isomer of 1-chloro-2,3,3-trifluoro-1-propene to a total amount of the Z-isomer of 1-chloro-2,3,3-trifluoro-1-propene and the E-isomer of 1-chloro-2,3,3-trifluoro-1-propene is 80 mass % or more and less than 100 mass %.

5. The solvent composition of claim 1, wherein a boiling point of the stabilizer is 30 to 120° C.

6. The solvent composition of claim 5,
   wherein the stabilizer further comprises at least one selected from methanol, ethanol, isopropanol, 2-propyn-1-ol, 1,2-butylene oxide, tetrahydrofuran, 1,4-dioxane, n-propylamine, diisopropylamine, N-methylmorpholine, N-methylpyrrole, and n-heptane.

7. A cleaning method comprising contacting an article to be cleaned with the solvent composition of claim 1.

8. The cleaning method of claim 7, wherein the article to be cleaned is at least one selected from a fiber product, a medical appliance, electric equipment, a precision instrument, and an optical article.

9. A method of forming a coating film, the method comprising:
dissolving a nonvolatile substance in the solvent composition of claim 1, to obtain a composition,
coating the obtained composition on an article to be coated, to obtain a coated composition, and
evaporating the coated composition, to form a coating film comprising the nonvolatile substance as a main component.

10. A heat transfer fluid, comprising the solvent composition of claim 1.

11. A heat cycle system, comprising the heat transfer fluid of claim 10.

12. The solvent composition of claim 1, wherein the unsaturated hydrocarbon comprises a butene isomer, a pentene isomer, a hexene isomer, a heptene isomer, an octene isomer, a nonene isomer, a diene compound and/or an unsaturated cyclic compound.

13. The solvent composition of claim 1, wherein a content of the unsaturated hydrocarbon is from 0.001 to 1 mass % in the solvent composition (100 mass %).

14. The solvent composition of claim 1, wherein the unsaturated hydrocarbon comprises 2-methyl-2-butene, 2-methyl-1-pentene, 2-methyl-2-pentene, 3-ethyl-2-butene, 2,3-dimethyl-2-butene, 2,4,4-trimethyl-1-pentene and/or 2,4,4-trimethyl-2-pentene.

15. The solvent composition of claim 1, wherein a content of the unsaturated hydrocarbon is from 1 mass ppm to 5 mass % in the solvent composition (100 mass %).

16. The solvent composition of claim 1, wherein a content of the unsaturated hydrocarbon is from 1 mass ppm to 1 mass % in the solvent composition (100 mass %).

17. The solvent composition of claim 1, wherein a content of the unsaturated hydrocarbon is from 0.001 to 5 mass % in the solvent composition (100 mass %).

* * * * *